(12) United States Patent
Craighead et al.

(10) Patent No.: US 12,303,899 B2
(45) Date of Patent: May 20, 2025

(54) SYSTEMS AND METHODS FOR ON-CHIP ANALYSIS OF NUCLEIC ACIDS AND FOR MULTIPLEXED ANALYSIS OF CELLS

(71) Applicant: CORNELL UNIVERSITY, Ithaca, NY (US)

(72) Inventors: Harold G. Craighead, Ithaca, NY (US); Harvey C. Tian, Ithaca, NY (US); David M. Lin, Ithaca, NY (US); Adam J. Bisogni, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 941 days.

(21) Appl. No.: 17/298,507

(22) PCT Filed: Nov. 29, 2019

(86) PCT No.: PCT/US2019/063887
§ 371 (c)(1),
(2) Date: May 28, 2021

(87) PCT Pub. No.: WO2020/113192
PCT Pub. Date: Jun. 4, 2020

(65) Prior Publication Data
US 2022/0016629 A1 Jan. 20, 2022

Related U.S. Application Data

(60) Provisional application No. 62/772,618, filed on Nov. 28, 2018, provisional application No. 62/772,620, filed on Nov. 28, 2018.

(51) Int. Cl.
*B01L 3/00* (2006.01)
*C12Q 1/6837* (2018.01)

(52) U.S. Cl.
CPC ...... *B01L 3/502761* (2013.01); *C12Q 1/6837* (2013.01); *B01L 2200/0668* (2013.01);
(Continued)

(58) Field of Classification Search
CPC ....... B01L 3/502761; B01L 2200/0668; B01L 2300/0819; B01L 2300/0887;
(Continued)

(56) References Cited

U.S. PATENT DOCUMENTS 5,304,487 A  4/1994 Wilding et al.
6,696,022 B1  2/2004 Chan et al.
(Continued)

FOREIGN PATENT DOCUMENTS

EP  2714884 A1  4/2014
WO  2007050040 A1  5/2007
(Continued)

OTHER PUBLICATIONS

Petralia et al., "A novel miniaturized biofilter based on silicon micropillars for nucleic acid extraction", 2017, Analyst, vol. 142, pp. 140-146 (Year: 2017).*
(Continued)

*Primary Examiner* — John McGuirk
(74) *Attorney, Agent, or Firm* — FisherBroyles, LLP; Andrew K. Gonsalves

(57) ABSTRACT

A microfluidic chip for on-chip detection of the presence or absence of a target nucleic acid region in an isolated nucleic acid sample is disclosed. The microfluidic chip includes a nucleic acid entanglement array, an isolated nucleic acid sample immobilized in the nucleic acid entanglement array, and at least one probe specific to a target nucleic acid region. Systems and methods of using the microfluidic chip are disclosed. An integrated microfluidic cell processing system is disclosed, which includes: a multiplexed microfluidic flow
(Continued)

directing system having a plurality of reconfigurable microfluidic layers that form a plurality of reconfigurable microfluidic channels, where the multiplexed microfluidic flow directing system function to assist in directing flow of materials into, through, and out of the integrated cell processing system; and at least one microfluidic chip functionally integrated into at least one layer of the multiplexed microfluidic flow directing system, and operates under continuous flow conditions.

20 Claims, 10 Drawing Sheets

(52) U.S. Cl.
CPC .................. B01L 2300/0819 (2013.01); B01L 2300/0887 (2013.01); B01L 2300/123 (2013.01); B01L 2400/086 (2013.01)

(58) Field of Classification Search
CPC ......... B01L 2300/123; B01L 2400/086; B01L 2300/0636; B01L 3/5025; C12Q 1/6837; B01D 15/1885; B01D 15/24; B01D 15/3804
See application file for complete search history.

(56) References Cited

U.S. PATENT DOCUMENTS

| | | | |
|---|---|---|---|
| 6,977,148 | B2 | 12/2005 | Dean et al. |
| 7,384,561 | B2 | 6/2008 | Utsunomiya |
| 7,964,978 | B1 | 6/2011 | Lee et al. |
| 8,562,918 | B2 | 10/2013 | Jovanovich et al. |
| 8,871,446 | B2 | 10/2014 | Hong et al. |
| 9,086,406 | B2 | 7/2015 | Lee et al. |
| 9,128,091 | B2 | 9/2015 | Toner et al. |
| 9,250,242 | B2 | 2/2016 | Martin et al. |
| 9,506,845 | B2 | 11/2016 | Fowler et al. |
| 9,803,192 | B2 | 10/2017 | Craighead et al. |
| 9,926,552 | B2 | 3/2018 | Craighead et al. |
| 2002/0081744 | A1 | 6/2002 | Chan et al. |
| 2002/0125192 | A1 | 9/2002 | Lopez et al. |
| 2003/0143599 | A1 | 7/2003 | Makarov et al. |
| 2003/0162181 | A1 | 8/2003 | Yang et al. |
| 2004/0050700 | A1 | 3/2004 | Lopez-Canovas et al. |
| 2004/0053403 | A1 | 3/2004 | Jedrzejewski et al. |
| 2004/0142491 | A1 | 7/2004 | Indermuhle et al. |
| 2005/0019819 | A1 | 1/2005 | Tooke et al. |
| 2005/0064575 | A1 | 3/2005 | Belgrader et al. |
| 2005/0069459 | A1 | 3/2005 | Ahn et al. |
| 2006/0133957 | A1 | 6/2006 | Knapp et al. |
| 2007/0077547 | A1 | 4/2007 | Shvets et al. |
| 2007/0218459 | A1* | 9/2007 | Miller .................. C12Q 1/6837 435/6.16 |
| 2008/0124721 | A1 | 5/2008 | Fuchs et al. |
| 2008/0124779 | A1 | 5/2008 | Oh et al. |
| 2008/0125330 | A1 | 5/2008 | Cady et al. |
| 2008/0160602 | A1 | 6/2008 | He et al. |
| 2008/0274905 | A1 | 11/2008 | Greene |
| 2009/0098541 | A1 | 4/2009 | Southern et al. |
| 2009/0186776 | A1 | 7/2009 | Webb et al. |
| 2009/0191563 | A1 | 7/2009 | Steemers et al. |
| 2010/0047924 | A1 | 2/2010 | Webster et al. |
| 2010/0137163 | A1 | 6/2010 | Link et al. |
| 2010/0190146 | A1 | 7/2010 | Bynum et al. |
| 2011/0014605 | A1 | 1/2011 | Stone |
| 2011/0027873 | A1 | 2/2011 | Cho et al. |
| 2011/0212440 | A1 | 9/2011 | Viovy et al. |
| 2011/0301058 | A1 | 12/2011 | Cheng et al. |
| 2012/0091235 | A1 | 4/2012 | Li et al. |
| 2014/0154703 | A1 | 6/2014 | Skelley et al. |
| 2014/0193812 | A1 | 7/2014 | Hamilton et al. |
| 2014/0194313 | A1 | 7/2014 | Craighead et al. |
| 2015/0018226 | A1 | 1/2015 | Hansen et al. |
| 2015/0099642 | A1 | 4/2015 | Barany et al. |
| 2015/0166987 | A1 | 6/2015 | Craighead et al. |
| 2017/0021353 | A1* | 1/2017 | Jiao .................. G01N 33/5302 |
| 2018/0305682 | A1 | 10/2018 | Craighead et al. |

FOREIGN PATENT DOCUMENTS

| | | | |
|---|---|---|---|
| WO | 2011017677 | A2 | 2/2011 |
| WO | 2011017681 | A2 | 2/2011 |
| WO | 2011038241 | A1 | 3/2011 |
| WO | 2012162779 | A1 | 12/2012 |
| WO | 2014153071 | A1 | 9/2014 |
| WO | 2015077441 | A2 | 5/2015 |
| WO | 2016154302 | A1 | 9/2016 |
| WO | 2017004463 | A1 | 1/2017 |
| WO | 2017205267 | A1 | 11/2017 |
| WO | 2017205304 | A1 | 11/2017 |

OTHER PUBLICATIONS

Zhang et al., "Aptamers selected by cell-SELEX for application in cancer studies," Bioanalysis, 2(5):907-918 (2010).
Dickey et al., "Oligonucleotide aptamers: A next-generation technology for the capture and detection of circulating tumor cells," Methods, 97:94-103 (2016).
Wan et al., "Capture, isolation and release of cancer cells with aptamer-functionalized glass bead array," Lab Chip, 12:4693-4701 (2012).
Phillips et al., "Enrichment of Cancer Cells Using Aptamers Immobilized on a Microfluidic Channel," Anal. Chem., 81:1033-1039 (2009).
Zheng et al., "Aptamer-Functionalized Barcode Particles for the Capture and Detection of Multiple Types of Circulating Tumor Cells," Adv. Mater., 26:7333-7338 (2014).
Xu et al., "Aptamer-Based Microfluidic Device for Enrichment, Sorting, and Detection of Multiple Cancer Cells," Anal. Chem., 81:7436-7442 (2009).
Sheng et al., "Aptamer-Enabled Efficient Isolation of Cancer Cells from Whole Blood Using a Microfluidic Device," Anal. Chem., 84:4199-4206 (2012).
Shen et al., "Specific Capture and Release of Circulating Tumor Cells Using Aptamer-Modified Nanosubstrates," Adv. Mater., 25:2368-2373 (2013).
Chen et al., "Targeted isolation and analysis of single tumor cells with aptamer-encoded microwell array on microfluidic device," Lab Chip, 12:5180-5185 (2012).
Liu et al., "Rare cell chemiluminescence detection based on aptamer-specific capture in microfluidic channels," Biosensors and Bioelectronics, 28:438-442 (2011).
Lin et al., "Assay of multiplex proteins from cell metabolism based on tunable aptamer and microchip electrophoresis," Biosensors and Bioelectronics, 63:105-111 (2015).
Martin et al., "Capturing cancer cells using aptamer-immobilized square capillary channels," Mol. BioSyst., 7:1720-1727 (2011).
Cabodi et al., "Entropic Recoil Separation of Long DNA Molecules," Anal. Chem., 74:5169-5174 (2002).
Benitez et al., "Microfluidic Extraction, Stretching and Analysis of Human Chromosomal DNA from Single Cells," Lab Chip, 12(22):4848-4854 (Nov. 21, 2012).
Saad et al., "Epidermal growth factor receptor T790M mutation-positive metastatic non-small-cell lung cancer: focus on osimertinib (AZD9291)," OncoTargets and Therapy, 10:1757-1766 (2017).
European Patent Office, Extended European Search Report issued in the counterpart European Application No. EP 1989162.7, dated Jul. 8, 2022.
International Searching Authority (USPTO), International Search Report and Written Opinion issued in counterpart PCT/US2019/063887, dated Apr. 8, 2020.

* cited by examiner

Gasket allows for flow directionality through the channels within the gasket layers. The channels themselves contain the micropillar arrays.

Design can be modified for single or multi-cell loading

FLUID FLOW DIRECTION

SYSTEMS AND METHODS FOR ON-CHIP ANALYSIS OF NUCLEIC ACIDS AND FOR MULTIPLEXED ANALYSIS OF CELLS

CROSS-REFERENCE TO RELATED APPLICATIONS

This application is a U.S. National Phase filing under 35 U.S.C. § 371 of International Application No. PCT/US2019/063887, filed Nov. 29, 2019, and published as WO 2020/113192 A1 on Jun. 4, 2020, which claims priority benefit of U.S. Provisional Patent Application Ser. No. 62/772,618, filed Nov. 28, 2018, and U.S. Provisional Patent Application Ser. No. 62/772,620, filed Nov. 28, 2018, the disclosures of which are hereby incorporated by reference herein in their entirety.

FIELD OF THE DISCLOSURE

The present disclosure relates to, inter alia, microfluidic and integrated microchannel technologies for use in systems and methods for on-chip analysis of nucleic acids and in cell processing systems while under flow conditions.

BACKGROUND OF THE DISCLOSURE

Various medical and life science based technologies rely on the isolation and analysis of various types of cells, particularly in relation to the functions of the cells and their genomic material. Cancer cells are of particular importance. Cancer cells contain genetic mutations that allow them to escape the regulatory processes necessary for the healthy function of tissues and organs. Moreover, there are numerous mechanisms for malignancy with different combinations of genetic mutations, and cancer cells are constantly evolving, which makes cancer treatment difficult with varying levels of efficacy. Many assays have been developed that detect specific mutations, whereas some have been designed to detect all mutations via sequencing. Each of these approaches has advantages and disadvantages. Most of these assays also require significant sample preparation to be performed in a bulk solution where the initial amount of genetic material is limited, some is lost in processing, and the remaining material is used up quickly. Therefore, an assay that incorporates sample preparation and enables the original genetic template to be reused would be highly advantageous.

Genetic mutations in cancer cells are not only fundamental to the disease, but can also have tremendous impact on the efficacy of treatment. Identification of specific key mutations in a timely and cost-effective way would allow clinicians to better prescribe the most effective treatment options. Furthermore, cancer cells are constantly evolving, so regular testing of multiple important genes is also beneficial for monitoring disease progression and future treatment.

Cancer therapeutics have evolved over the last two decades. Clinicians now understand that to provide cancer patients with effective treatments, a more personalized approach to medicine must be adopted. For many cancers, chemotherapy drugs are not administered to the patient until the patient has undergone genetic testing. This is because certain mutations in their genome can cause specific cancer drugs to either be ineffective, or more effective than in patients without the mutations. An example of this is the T790M mutation in lung cancer, where patients who have the mutation will often develop drug resistance to epidermal growth factor receptor (EGFR) inhibiting chemotherapy agents such as gefitinib and erlotinib. In such cases, EGFR T790M lung cancer patients are prescribed Osimertinib, an FDA-approved drug with high potency against T790M mutants.

These key mutations that can affect treatment strategy are known as therapeutically actionable (TA) mutations. Identifying TA-mutations rapidly and accurately is critical for improved patient outcomes. Currently, clinicians rely on targeted DNA amplification and then DNA sequencing to check for TA-mutations in cancer patients. This is not only a laborious and expensive process that requires patient sample to be transferred to a separate laboratory, the turn-around time to get answers on the presence or absence of key TA-mutations can take days or even weeks. This is critical time that the patient must wait before entering treatment, during which the cancer is progressing in their bodies.

There is a need for new and improved technologies for studying cancer and other genetic disorders, and particularly for detecting and understanding genetic mutations implicated in various cancers. There is also a need for additional methods of detecting and treating cancer and other genetic disorders. There is also a need for efficient and sensitive assays and techniques for studying nucleic acid profiles of subjects.

The present invention is directed to overcoming these and other deficiencies in the art.

SUMMARY

The present invention relates to, inter alia, a combination of on-chip microfluidic and microchannel technologies suitable for use in studying, analyzing, detecting, and treating various conditions and diseases.

In one aspect, the present disclosure provides a microfluidic chip for on-chip detection of a presence or absence of a target nucleic acid region in an isolated nucleic acid sample. The microfluidic chip includes: (a) a nucleic acid entanglement array having a plurality of nucleic acid entanglement micropillars configured and arranged in a manner effective to physically entangle and maintain thereon an isolated nucleic acid sample; (b) the isolated nucleic acid sample immobilized in the nucleic acid entanglement array; and (c) at least one probe specific to a target nucleic acid region, the at least one probe being specifically bound to the target nucleic acid region and detectable when the isolated nucleic acid sample includes the target nucleic acid region, thereby enabling on-chip analysis of the presence or absence of the target nucleic acid region in the isolated nucleic acid sample.

In another aspect, the present disclosure relates to a microfluidic system for on-chip detection of a presence or absence of a target nucleic acid region in an isolated nucleic acid sample. The system includes: (a) an input controller component for introducing fluids, cells, reagents, and probes into the system under flow conditions; (b) a collection reservoir for collecting materials exported out of the system; (c) at least one microfluidic chip according to those described and contemplated herein, where the at least one microfluidic chip is detachably connected to the fluid controller by a fluidic input port and detachably connected to the collection reservoir by an output port; and (d) a detection component effective for on-chip detection of the presence or absence of the target nucleic acid region in the isolated nucleic acid sample immobilized on the at least one microfluidic chip.

In another aspect, the present disclosure provides a method for on-chip detection of a presence or absence of a target nucleic acid region in an isolated nucleic acid sample. This method involves the steps of: providing a microfluidic system as described or contemplated herein; and operating the microfluidic system in a manner sufficient to conduct on-chip detection of the presence or absence of a target nucleic acid region in an isolated nucleic acid sample.

In another aspect, the present disclosure provides an integrated microfluidic cell processing system. The integrated microfluidic cell processing system includes: a multiplexed microfluidic flow directing system having a plurality of reconfigurable microfluidic layers that form a plurality of reconfigurable microfluidic channels, where the multiplexed microfluidic flow directing system function to assist in directing flow of materials into, through, and out of the integrated cell processing system; and at least one microfluidic chip functionally integrated into at least one layer of the multiplexed microfluidic flow directing system, where the at least one microfluidic chip comprises a cell capture component and a nucleic acid entanglement component, and where the integrated microfluidic device operates under continuous flow conditions to process one or more cell.

In another aspect, the present disclosure provides a method of collecting one or more liquid sample from an affinity chromatography microcolumn for further analysis. This method involves the steps of: providing an integrated microfluidic cell processing system described and/or contemplated herein; running one or more liquid sample through the microcolumns of the device of the system either in a parallel manner or a serial manner under conditions effective to allow a test agent contained in the liquid sample to bind specifically to a target molecule contained in the microcolumn of the device; and recovering from each microcolumn the test agent or test agents that bind specifically to the respective target molecules of each microcolumn device, the recovering taking place in the liquid collection apparatus.

Various aspects of the present disclosure are also addressed by the following Paragraphs 1-105 and in the noted combinations thereof, as follows:

Paragraph 1: A microfluidic chip for on-chip detection of a presence or absence of a target nucleic acid region in an isolated nucleic acid sample, said microfluidic chip comprising: (a) a nucleic acid entanglement array comprising a plurality of nucleic acid entanglement micropillars configured and arranged in a manner effective to physically entangle and maintain thereon an isolated nucleic acid sample; (b) the isolated nucleic acid sample immobilized in the nucleic acid entanglement array; and (c) at least one probe specific to a target nucleic acid region, said at least one probe being specifically bound to the target nucleic acid region and detectable when said isolated nucleic acid sample includes the target nucleic acid region, thereby enabling on-chip analysis of the presence or absence of the target nucleic acid region in the isolated nucleic acid sample.

Paragraph 2: The microfluidic chip according to Paragraph 1, wherein the isolated nucleic acid sample comprises genomic DNA (gDNA), extrachromosomal DNA, chromatin, plasmid DNA, a nucleic acid aptamer, an oligonucleotide, and a nucleic acid biomarker.

Paragraph 3: The microfluidic chip according to Paragraph 1, wherein the isolated nucleic acid sample comprises single-stranded DNA, double-stranded DNA, or a combination of both single- and double-stranded DNA.

Paragraph 4: The microfluidic chip according to Paragraph 1, wherein the target nucleic acid region comprises a gene, mutation, or nucleotide sequence from a eukaryotic cell.

Paragraph 5: The microfluidic chip according to Paragraph 1, wherein the target nucleic acid region comprises a gene, mutation, or nucleotide sequence from an animal.

Paragraph 6: The microfluidic chip according to Paragraph 5, wherein the target nucleic acid region comprises a gene, mutation, or nucleotide sequence from a human or non-human animal.

Paragraph 7: The microfluidic chip according to Paragraph 1, wherein the target nucleic acid region comprises a gene, mutation, or nucleotide sequence that is related to or that is a marker for presence or risk of a disease or abnormal condition of a multicellular organism.

Paragraph 8: The microfluidic chip according to Paragraph 7, wherein the disease or abnormal condition is a human disease selected from the group consisting of cancer, Down's syndrome, Huntington's disease, heart disease, thalassemia, cystic fibrosis, tay-sachs disease, sickle cell anemia, marfan syndrome, fragile X syndrome, hemochromatosis, and the like, or a canine disease selected from the group consisting of hip dysplasia, urinary bladder stones, epilepsy, heart disease, degenerative myelopathy, brachycephalic syndrome, and the like.

Paragraph 9: The microfluidic chip according to Paragraph 8, wherein the disease is cancer and the mutation is a therapeutically-actionable (TA) mutation.

Paragraph 10: The microfluidic chip according to Paragraph 1, wherein the isolated nucleic acid sample is isolated from one or more cell.

Paragraph 11: The microfluidic chip according to Paragraph 1, wherein the target nucleic acid region is specific for a pathogen, antibiotic resistant strain of bacteria, food contaminant, foodborne illness, paternity determination, DNA fingerprinting, or individual identity.

Paragraph 12: The microfluidic chip according to Paragraph 1, wherein the at least one probe comprises a collection of multiple probes with each probe being specific to a unique target nucleic acid region or to another probe which is specific to a unique target nucleic acid region.

Paragraph 13: The microfluidic chip according to Paragraph 12, wherein the collection of multiple probes comprises a panel of probes effective to produce a genetic profile for a disease or abnormal condition in a multicellular organism.

Paragraph 14: The microfluidic chip according to Paragraph 1, wherein the probe is a fluorescence probe.

Paragraph 15: The microfluidic chip according to Paragraph 1, wherein the probe is selected from the group consisting of molecular beacons, peptide nucleic acid probes, aptamers, and protein probes.

Paragraph 16: A microfluidic system for on-chip detection of a presence or absence of a target nucleic acid region in an isolated nucleic acid sample, said system comprising: (a) an input controller component for introducing fluids, cells, reagents, and probes into the system under flow conditions; (b) a collection reservoir for collecting materials exported out of the system; (c) at least one microfluidic chip according to any one of Paragraphs 1-15, wherein said at least one microfluidic chip is detachably connected to the fluid controller by a fluidic input port and detachably connected to the collection reservoir by an output port; and (d) a detection component effective for on-chip detection of the presence or absence of the target nucleic acid region in the isolated nucleic acid sample immobilized on the at least one microfluidic chip.

Paragraph 17: The microfluidic system according to Paragraph 16 further comprising: a multiplexed microfluidic flow directing system comprising a plurality of reconfigurable microfluidic layers that form a plurality of reconfigurable microfluidic channels, wherein said multiplexed microfluidic flow directing system functions to assist in directing flow of materials into the microfluidic system, through the microfluidic system, and out of the microfluidic system.

Paragraph 18: The microfluidic system according to Paragraph 17, wherein the at least one microfluidic chip is functionally integrated with the multiplexed microfluidic flow directing system.

Paragraph 19: The microfluidic system according to Paragraph 18, wherein the at least one microfluidic chip is integrated with the multiplexed microfluidic flow directing system in a manner so that flow of materials into the microfluidic system is directed into and through the at least one microfluidic chip before being exported from the microfluidic system.

Paragraph 20: The microfluidic system according to Paragraph 17, wherein the multiplexed microfluidic flow directing system is configured to receive and export one or more sample in manual and/or automated fashion.

Paragraph 21: The microfluidic system according to Paragraph 20, wherein the multiplexed microfluidic flow directing system is configured to receive the one or more sample via one or more pipette.

Paragraph 22: The microfluidic system according to Paragraph 17, wherein the multiplexed microfluidic flow directing system is configured to assist in sorting materials for export from the microfluidic system for further collection, purification, and/or analysis.

Paragraph 23: A method for on-chip detection of a presence or absence of a target nucleic acid region in an isolated nucleic acid sample, said method comprising the steps of: providing a microfluidic system according to Paragraph 16; and operating the microfluidic system in a manner sufficient to conduct on-chip detection of the presence or absence of a target nucleic acid region in an isolated nucleic acid sample.

Paragraph 24: The method according to Paragraph 23, wherein the step of operating the microfluidic system comprises the steps of: introducing at least one cell of interest into the microfluidic system using the input controller component under conditions sufficient to (i) capture the at least one cell of interest; (ii) extract gDNA from the captured at least one cell of interest; and (iii) isolate and immobilize the gDNA in the nucleic acid entanglement micropillars of the microfluidic chip; providing at least one probe specific to the target nucleic acid region and introducing the at least one probe into the microfluidic system using hydrodynamic flow and under conditions sufficient to allow the at least one probe to contact and specifically bind to the isolated and immobilized gDNA if the target nucleic acid region is present in the gDNA; and using the detection component for on-chip detection of the presence or absence of the target nucleic acid region in the isolated and immobilized gDNA.

Paragraph 25: The method according to Paragraph 23, wherein the isolated nucleic acid sample comprises genomic DNA (gDNA), extrachromosomal DNA, chromatin, plasmid DNA, a nucleic acid aptamer, an oligonucleotide, and a nucleic acid biomarker.

Paragraph 26: The method according to Paragraph 23, wherein the isolated nucleic acid sample comprises single-stranded DNA, double-stranded DNA, or a combination of both single- and double-stranded DNA.

Paragraph 27: The method according to Paragraph 23, wherein the target nucleic acid region comprises a gene, mutation, or nucleotide sequence from a eukaryotic cell.

Paragraph 28: The method according to Paragraph 23, wherein the target nucleic acid region comprises a gene, mutation, or nucleotide sequence from an animal.

Paragraph 29: The method according to Paragraph 28, wherein the target nucleic acid region comprises a gene, mutation, or nucleotide sequence from a human or non-human animal.

Paragraph 30: The method according to Paragraph 23, wherein the target nucleic acid region comprises a gene, mutation, or nucleotide sequence that is related to or that is a marker for presence or risk of a disease or abnormal condition of a multicellular organism.

Paragraph 31: The method according to Paragraph 30, wherein the disease or abnormal condition is selected from the group consisting of a human disease selected from the group consisting of cancer, Down's syndrome, Huntington's disease, heart disease, thalassemia, cystic fibrosis, tay-sachs disease, sickle cell anemia, marfan syndrome, fragile X syndrome, hemochromatosis, and the like, or a canine disease selected from the group consisting of hip dysplasia, urinary bladder stones, epilepsy, heart disease, degenerative myelopathy, brachycephalic syndrome, and the like.

Paragraph 32: The method according to Paragraph 31, wherein the disease is cancer and the mutation is a therapeutically-actionable (TA) mutation.

Paragraph 33: The method according to Paragraph 23, wherein the isolated nucleic acid sample is isolated from one or more cell.

Paragraph 34: The method according to Paragraph 23, wherein the target nucleic acid region is specific for a pathogen, antibiotic resistant strain of bacteria, food contaminant, foodborne illness, paternity determination, DNA fingerprinting, or individual identity.

Paragraph 35: The method according to Paragraph 23, wherein the at least one probe comprises a collection of multiple probes with each probe being specific to a unique target nucleic acid region or to another probe which is specific to a unique target nucleic acid region.

Paragraph 36: The method according to Paragraph 35, wherein the collection of multiple probes comprises a panel of probes effective to produce a genetic profile for a disease or abnormal condition in a multicellular organism.

Paragraph 37: The method according to Paragraph 23, wherein the probe is a fluorescence probe.

Paragraph 38: The method according to Paragraph 23, wherein the probe is selected from the group consisting of molecular beacons, peptide nucleic acid probes, aptamers, and protein probes.

Paragraph 39: The method according to Paragraph 23, wherein the microfluidic system further comprises: a multiplexed microfluidic flow directing system comprising a plurality of reconfigurable microfluidic layers that form a plurality of reconfigurable microfluidic channels, wherein said multiplexed microfluidic flow directing system functions to assist in directing flow of materials into the microfluidic system, through the microfluidic system, and out of the microfluidic system.

Paragraph 40: The method according to Paragraph 39, wherein the at least one microfluidic chip is functionally integrated with the multiplexed microfluidic flow directing system.

Paragraph 41: The method according to Paragraph 39, wherein the at least one microfluidic chip is integrated with the multiplexed microfluidic flow directing system in a manner so that flow of materials into the microfluidic system is directed into and through the at least one microfluidic chip before being exported from the microfluidic system.

Paragraph 42: The method according to Paragraph 39, wherein the multiplexed microfluidic flow directing system is configured to receive and export one or more sample in manual and/or automated fashion.

Paragraph 43: The method according to Paragraph 42, wherein the multiplexed microfluidic flow directing system is configured to receive the one or more sample via one or more pipette.

Paragraph 44: The method according to Paragraph 39, wherein the multiplexed microfluidic flow directing system is configured to assist in sorting materials for export from the microfluidic system for further collection, purification, and/or analysis.

Paragraph 45: An integrated microfluidic cell processing system, said system comprising: a multiplexed microfluidic flow directing system comprising a plurality of reconfigurable microfluidic layers that form a plurality of reconfigurable microfluidic channels, wherein said multiplexed microfluidic flow directing system function to assist in directing flow of materials into, through, and out of the integrated cell processing system; and at least one microfluidic chip functionally integrated into at least one layer of the multiplexed microfluidic flow directing system, wherein said at least one microfluidic chip comprises a cell capture component and a nucleic acid entanglement component, wherein the integrated microfluidic device operates under continuous flow conditions to process one or more cell.

Paragraph 46: The integrated microfluidic cell processing system according to Paragraph 45, wherein said cell capture component comprises a cell capture array comprising a plurality of cell capture micropillars, and wherein said nucleic acid entanglement component comprises a nucleic acid entanglement array comprising a plurality of nucleic acid entanglement micropillars.

Paragraph 47: The integrated microfluidic cell processing system according to Paragraph 45, wherein the at least one microfluidic chip is integrated with the multiplexed microfluidic flow directing system in a manner so that flow of materials into the microfluidic system is directed into and through the at least one microfluidic chip before being exported from the microfluidic system.

Paragraph 48: The integrated microfluidic cell processing system according to Paragraph 45, wherein the multiplexed microfluidic flow directing system is configured to receive and export one or more sample in manual and/or automated fashion.

Paragraph 49: The integrated microfluidic cell processing system according to Paragraph 48, wherein the multiplexed microfluidic flow directing system is configured to receive the one or more sample via one or more pipette.

Paragraph 50: The integrated microfluidic cell processing system according to Paragraph 45, wherein the multiplexed microfluidic flow directing system is configured to assist in sorting materials for export from the microfluidic system for further collection, purification, and/or analysis.

Paragraph 51: The integrated microfluidic cell processing system according to Paragraph 45, wherein the multiplexed microfluidic flow directing system comprises a multiplexed device configured for conducting affinity chromatography in multiple microcolumns in parallel and/or in series, said multiplexed device comprising: a microcolumn layer comprising a top surface, a bottom surface, and a plurality of substantially vertically aligned microcolumns for passing one or more sample liquids therethrough, said microcolumns extending from the top to the bottom surface of the microcolumn layer and optionally containing an affinity chromatography agent; a top capping layer proximately disposed at the top surface of the microcolumn layer and comprising a patterned grid having at least one opening in fluid alignment with at least one microcolumn so as to allow a sample liquid to pass through the top capping layer and into the microcolumn; and a bottom capping layer proximately disposed at the bottom surface of the microcolumn layer and comprising either a parallel patterned grid for running multiple liquid samples through the microcolumns in a parallel manner or a series patterned grid for passing a single liquid sample through multiple serially connected microcolumns in a serial manner.

Paragraph 52: The integrated microfluidic cell processing system according to Paragraph 51, wherein the microcolumn layer is made of a material selected from the group consisting of poly(methyl methacrylate) (PMMA), cyclic olefin copolymer, polyethylene, polypropylene, and polystyrene, or functional derivatives or variants thereof.

Paragraph 53: The integrated microfluidic cell processing system according to Paragraph 51, wherein the top capping layer and the bottom capping layer are made of a material selected from the group consisting of poly(methyl methacrylate) (PMMA), cyclic olefin copolymer, polyethylene, polypropylene, and polystyrene, or functional derivatives or variants thereof.

Paragraph 54: The integrated microfluidic cell processing system according to Paragraph 51, wherein the parallel patterned grid of the bottom capping layer comprises opening portions in fluid alignment with those microcolumns through which liquid samples are desired to pass in a parallel manner.

Paragraph 55: The integrated microfluidic cell processing system according to Paragraph 51, wherein the series patterned grid of the bottom capping layer further comprises a bottom channel layer having a plurality of substantially horizontal channel portions each forming a flow channel fluidly connecting adjacent microcolumns of the serially connected microcolumns through which the single liquid sample is desired to pass in a serial manner.

Paragraph 56: The integrated microfluidic cell processing system according to Paragraph 51 further comprising: a top channel layer disposed between the top capping layer and the top surface of the microcolumn layer, wherein the top channel layer comprises a plurality of substantially horizontal channel portions each forming a flow channel fluidly connecting adjacent microcolumns of the serially connected microcolumns through which the single liquid sample is desired to pass in a serial manner.

Paragraph 57: The integrated microfluidic cell processing system according to Paragraph 56, wherein the top channel layer is patterned to work in fluid and serial connection with the plurality of horizontal channel portions of the bottom capping layer so as to pass the single liquid sample through the serially connected microcolumns in a serial manner.

Paragraph 58: The integrated microfluidic cell processing system according to Paragraph 56, wherein the top channel layer is made of a material selected from the group consisting of silicone and rubber, or functional derivatives or variants thereof.

Paragraph 59: The integrated microfluidic cell processing system according to Paragraph 51 further comprising: a top port layer proximately disposed on the top capping layer, said top port layer comprising one or more input port each in fluidic alignment with a corresponding microcolumn so as to effectuate introduction of a sample liquid into a desired microcolumn.

Paragraph 60: The integrated microfluidic cell processing system according to Paragraph 59, wherein the top port layer further comprises at least one outlet port for expelling a liquid sample from one of the microcolumns after it passes through a plurality of serially connected microcolumns in serial manner.

Paragraph 61: The integrated microfluidic cell processing system according to Paragraph 59, wherein the ports of the top port layer are NanoPorts™, connectors, and/or tubing made of a material selected from the group consisting of a polymer, a thermoplastic polymer, and polyether ether ketone (PEEK), or functional derivatives or variants thereof.

Paragraph 62: The integrated microfluidic cell processing system according to Paragraph 51 further comprising: a bottom port layer proximately disposed on the bottom capping layer, said bottom port layer comprising one or more outlet port each in fluidic alignment with a corresponding microcolumn so as to effectuate expulsion of a liquid sample from a desired microcolumn.

Paragraph 63: The integrated microfluidic cell processing system according to Paragraph 62, wherein the ports of the bottom port layer are NanoPorts™, connectors, and/or tubing made of a material selected from the group consisting of a polymer, a thermoplastic polymer, and polyether ether ketone (PEEK), or functional derivatives or variants thereof.

Paragraph 64: The integrated microfluidic cell processing system according to Paragraph 51 further comprising: a top frit gasket layer and/or a bottom frit gasket layer for aiding the containment of an affinity chromatography agent within the microcolumns, wherein said top frit gasket layer is deposited between the top surface of the microcolumn layer and the top capping layer, and wherein the bottom frit gasket layer is deposited between the bottom surface of the microcolumn layer and the bottom capping layer.

Paragraph 65: The integrated microfluidic cell processing system according to Paragraph 64, wherein the top and bottom frit gasket layers are made of a material selected from the group consisting of silicone, rubber, a plastic polymer, polytetrafluoroethylene, paper, metal, cork, felt, neoprene, nitrile rubber, and fiberglass, or functional derivatives or variants thereof.

Paragraph 66: The integrated microfluidic cell processing system according to Paragraph 51 further comprising: a top port layer proximately disposed on the top capping layer, said top port layer comprising one or more input port each in fluidic alignment with a corresponding microcolumn so as to effectuate introduction of a sample liquid into a desired microcolumn; an optional bottom port layer proximately disposed on the bottom capping layer, said bottom port layer comprising one or more outlet port each in fluidic alignment with a corresponding microcolumn so as to effectuate expulsion of a liquid sample from a desired microcolumn; and a top washer layer and/or a bottom washer layer for securing the ports for the top port layer and the optional bottom port layer in alignment with their corresponding microcolumns, wherein said top washer layer is proximately deposited at the top capping layer and comprises a plurality of openings through which the ports of the top port layer protrude, and wherein said bottom washer layer is proximately deposited at the bottom capping layer and comprises a plurality of openings through which the ports of the optional bottom port layer protrude.

Paragraph 67: The integrated microfluidic cell processing system according to Paragraph 66, wherein the top and bottom washer layers are made of a material selected from the group consisting of poly(methyl methacrylate) (PMMA), cyclic olefin copolymer, polyethylene, polypropylene, and polystyrene, or functional derivatives thereof.

Paragraph 68: The integrated microfluidic cell processing system according to Paragraph 51, wherein the affinity chromatography agent is selected from the group consisting of a resin, a modified resin, and microbeads.

Paragraph 69: The integrated microfluidic cell processing system according to Paragraph 51, wherein the affinity chromatography agent comprises an immobilized target molecule.

Paragraph 70: The integrated microfluidic cell processing system according to Paragraph 69, wherein the immobilized target molecule is labeled.

Paragraph 71: The integrated microfluidic cell processing system according to Paragraph 69, wherein the immobilized target molecule is selected from the group consisting of a whole cell, a virus, a virus particle, a protein, a modified protein, a polypeptide, a modified polypeptide, an RNA molecule, a DNA molecule, a modified DNA molecule, a polysaccharide, an amino acid, an antibiotic, a pharmaceutical agent, an organic non-pharmaceutical agent, a macromolecular complex, a carbohydrate, a lipid, a small molecule, a chemical compound, a mixture of lysed cells, and a mixture of purified, partially purified, or non-purified protein.

Paragraph 72: The integrated microfluidic cell processing system according to Paragraph 71, wherein the immobilized target molecule is provided from a mixture of lysed cells, a mixture of purified, partially purified, or non-purified protein.

Paragraph 73: The integrated microfluidic cell processing system according to Paragraph 51, wherein the microcolumns have a volume capacity of between about 0.5 µL and about 250 µL.

Paragraph 74: The integrated microfluidic cell processing system according to Paragraph 51, wherein the affinity chromatography involves anion exchange technology, group exclusions, immobilized-metal affinity chromatography (IMAC), fusion tag protein purification, pull-down assays, or immunoprecipitations.

Paragraph 75: The integrated microfluidic cell processing system according to Paragraph 51, wherein the one or more liquid sample comprises one or more test agent for running through at least one of the microcolumns to determine its affinity or lack of affinity to the affinity chromatography agent.

Paragraph 76: The integrated microfluidic cell processing system according to Paragraph 75, wherein the test agent is selected from the group consisting of an aptamer, a protein, a protein complex, a modified protein, a polypeptide, a modified polypeptide, an RNA molecule, a DNA molecule, a modified DNA molecule, and a drug.

Paragraph 77: The integrated microfluidic cell processing system according to Paragraph 45, wherein said microfluidic chip is configured for on-chip detection of a presence or absence of a target nucleic acid region in an isolated nucleic acid sample, said microfluidic chip comprising: (a) a nucleic acid entanglement array comprising a plurality of nucleic acid entanglement micropillars configured and arranged in a manner effective to physically entangle and maintain thereon an isolated nucleic acid sample; (b) the isolated nucleic acid sample immobilized in the nucleic acid entanglement array; and (c) at least one probe specific to a target nucleic acid region, said at least one probe being specifically bound to the target nucleic acid region and detectable when said isolated nucleic acid sample includes the target nucleic acid region, thereby enabling on-chip analysis of the presence or absence of the target nucleic acid region in the isolated nucleic acid sample.

Paragraph 78: The integrated microfluidic cell processing system according to Paragraph 77, wherein the isolated nucleic acid sample comprises genomic DNA (gDNA), extrachromosomal DNA, chromatin, plasmid DNA, a nucleic acid aptamer, an oligonucleotide, and a nucleic acid biomarker.

Paragraph 79: The integrated microfluidic cell processing system according to Paragraph 77, wherein the isolated nucleic acid sample comprises single-stranded DNA, double-stranded DNA, or a combination of both single- and double-stranded DNA.

Paragraph 80: The integrated microfluidic cell processing system according to Paragraph 77, wherein the target nucleic acid region comprises a gene, mutation, or nucleotide sequence from a eukaryotic cell.

Paragraph 81: The integrated microfluidic cell processing system according to Paragraph 77, wherein the target nucleic acid region comprises a gene, mutation, or nucleotide sequence from an animal.

Paragraph 82: The integrated microfluidic cell processing system according to Paragraph 81, wherein the target nucleic acid region comprises a gene, mutation, or nucleotide sequence from a human or non-human animal.

Paragraph 83: The integrated microfluidic cell processing system according to Paragraph 77, wherein the target nucleic acid region comprises a gene, mutation, or nucleotide sequence that is related to or that is a marker for presence or risk of a disease or abnormal condition of a multicellular organism.

Paragraph 84: The integrated microfluidic cell processing system according to Paragraph 83, wherein the disease or abnormal condition is selected from the group consisting of a human disease selected from the group consisting of cancer, Down's syndrome, Huntington's disease, heart disease, thalassemia, cystic fibrosis, tay-sachs disease, sickle cell anemia, marfan syndrome, fragile X syndrome, hemochromatosis, and the like, or a canine disease selected from the group consisting of hip dysplasia, urinary bladder stones, epilepsy, heart disease, degenerative myelopathy, brachycephalic syndrome, and the like.

Paragraph 85: The integrated microfluidic cell processing system according to Paragraph 84, wherein the disease is cancer and the mutation is a therapeutically-actionable (TA) mutation.

Paragraph 86: The integrated microfluidic cell processing system according to Paragraph 77, wherein the isolated nucleic acid sample is isolated from one or more cell.

Paragraph 87: The integrated microfluidic cell processing system according to Paragraph 77, wherein the target nucleic acid region is specific for a pathogen, antibiotic resistant strain of bacteria, food contaminant, foodborne illness, paternity determination, DNA fingerprinting, or individual identity.

Paragraph 88: The integrated microfluidic cell processing system according to Paragraph 77, wherein the at least one probe comprises a collection of multiple probes with each probe being specific to a unique target nucleic acid region or to another probe which is specific to a unique target nucleic acid region.

Paragraph 89: The integrated microfluidic cell processing system according to Paragraph 88, wherein the collection of multiple probes comprises a panel of probes effective to produce a genetic profile for a disease or abnormal condition in a multicellular organism.

Paragraph 90: The integrated microfluidic cell processing system according to Paragraph 77, wherein the probe is a fluorescence probe.

Paragraph 91: The integrated microfluidic cell processing system according to Paragraph 77, wherein the probe is selected from the group consisting of molecular beacons, peptide nucleic acid probes, aptamers, and protein probes.

Paragraph 92: The integrated microfluidic cell processing system according any one of Paragraphs 45-91, said system being suitable for collecting one or more liquid sample from an affinity chromatography microcolumn device, said system further comprising: a liquid flow mechanism for moving a liquid sample into, through, and out of a microcolumn; and a liquid collection apparatus comprising well portions for collecting liquid samples from the microcolumns, wherein each well portion is aligned with a single corresponding microcolumn for collection of the liquid sample therefrom.

Paragraph 93: The integrated microfluidic cell processing system according to Paragraph 92, wherein the liquid flow mechanism is programmable to move the liquid samples through the microcolumns at a desired flow rate, at a desired volume, for a desired amount of time, and/or for a desired time interval.

Paragraph 94: The integrated microfluidic cell processing system according to Paragraph 92, wherein the liquid flow mechanism comprises a pump for either pushing or pulling the liquid sample through one or more of the microcolumns.

Paragraph 95: The integrated microfluidic cell processing system according to Paragraph 94, wherein the pump controls flow rate of the liquid samples through the microcolumns.

Paragraph 96: The integrated microfluidic cell processing system according to Paragraph 92, wherein the liquid collection apparatus is a microplate having a plurality of wells for collecting liquid samples from the microcolumns.

Paragraph 97: The integrated microfluidic cell processing system according to Paragraph 96, wherein the microplate comprises a number of wells selected from the group consisting of 6, 12, 24, 48, 96, 384, 1536, 3456, and 9600 wells.

Paragraph 98: A method of collecting one or more liquid sample from an affinity chromatography microcolumn for further analysis, said method comprising: providing an integrated microfluidic cell processing system according to Paragraph 92; running one or more liquid sample through the microcolumns of the device of the system either in a parallel manner or a serial manner under conditions effective to allow a test agent contained in the liquid sample to bind specifically to a target molecule contained in the microcolumn of the device; and recovering from each microcolumn the test agent or test agents that bind specifically to the respective target molecules of each microcolumn device, said recovering taking place in the liquid collection apparatus.

Paragraph 99: The method according to Paragraph 98, wherein the recovering step comprises: washing unbound and weakly bound test agents from each microcolumn; and eluting the test agents that specifically bind to the target molecules of each microcolumn.

Paragraph 100: The method according to Paragraph 98, wherein the recovered test agents that specifically bind to the target molecules are nucleic acid aptamers comprising RNA aptamers, the method further comprising: performing reverse transcription amplification of the selected aptamer population.

Paragraph 101: The method according to Paragraph 98 further comprising: purifying and sequencing the amplified aptamer population.

Paragraph 102: The method according to Paragraph 101, wherein said recovering, said performing reverse transcription amplification, said purifying, and/or said sequencing are performed in one or more separate fluidic devices coupled in fluidic communication with the microcolumn devices.

Paragraph 103: The method according to Paragraph 98, wherein each of said running and recovering is automated.

Paragraph 104: The method according to Paragraph 98, wherein said liquid samples collected from the microcolumns are further used in analytical processes.

Paragraph 105: The method according to Paragraph 104, wherein said analytical processes comprise high throughput processes, quantitative polymerase chain reaction (qPCR), UV-Visual absorption spectroscopy, fluorescence spectroscopy, nucleic acid sequencing, and mass spectrometry.

These and other objects, features, and advantages of this invention will become apparent from the following detailed description of the various aspects of the invention taken in conjunction with the accompanying drawings.

BRIEF DESCRIPTION OF THE DRAWINGS

FIG. 2A illustrates gDNA that has already been extracted and immobilized onto the micropillars from mouse cells (3T3 cell line). FIG. 2B illustrates gDNA that has already been extracted and immobilized onto the micropillars from human cancer cells (HeLa cell line).

FIG. 3A illustrates an exploded view, a cross-sectional view, and a perspective view of the system. FIG. 3B illustrates an exploded view, a cross-sectional view, and a perspective view of the system, and further showing the fluid flow direction through the system. FIG. 3C illustrates a gasket layer and a close-up of a port and channel portion of the system. FIG. 3D illustrates a gasket layer and a close-up of a port and channel portion of the system, and further showing the fluid flow direction through the port and channel portion of the system.

FIG. 4A illustrates an exploded view, a cross-sectional view, and a perspective view of the system. FIG. 4B illustrates an exploded view, a cross-sectional view, and a perspective view of the system, and further showing the fluid flow direction through the system. FIG. 4C illustrates a gasket layer and a close-up of a port and channel portion of the system. FIG. 4D illustrates a gasket layer and a close-up of a port and channel portion of the system, and further showing the fluid flow direction through the port and channel portion of the system.

DETAILED DESCRIPTION

Figure 1:
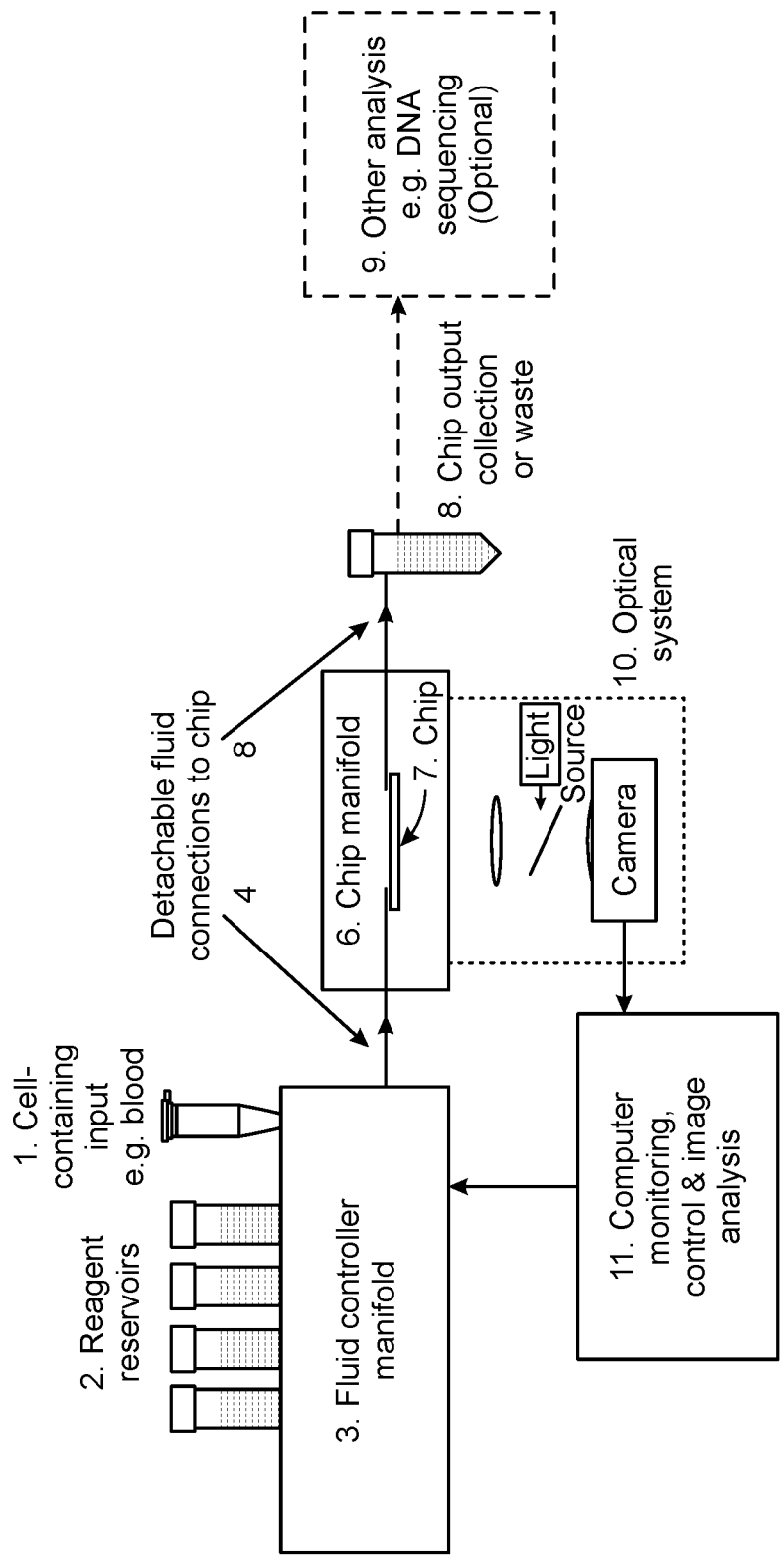
FIG. 1 is a schematic of one embodiment of a microfluidic system according to the present disclosure for on-chip detection of the presence or absence of a target nucleic acid region in an isolated nucleic acid sample.

The present disclosure relates to, inter alia, microfluidic, micropillar, and integrated microchannel technologies for use in devices, systems, and methods for on-chip analysis of nucleic acids and in cell processing systems while under flow conditions. The devices, systems, and methods of the present disclosure are suitable for use in studying, analyzing, detecting, and treating various conditions and diseases. More particularly, the devices, systems, and methods of the present disclosure are suitable for use in analyzing isolated nucleic acid samples from a cell sample for target nucleic acid regions. Further, the devices, systems, and methods of the present disclosure are suitable for efficiently processing cells for purposes of isolating nucleic acid samples and other cellular materials for on-chip and/or off-chip analysis.

The present disclosure provides, inter alia, a devices, systems, and methods for rapid and sensitive biochemical analysis of selected cells utilizing a microfluidic device coupled to a variety of analytical and control systems. Microstructures incorporated in the microfluidic device can capture and isolate cells by size, deformability, or by affinity binding. This can be used to separate cells of interest from complex mixtures or biological fluids such as blood or environmental samples such as drinking water. The devices, systems, and methods of the present disclosure enable the rapid and sensitive analysis of these cells (including rare cells) by a variety of analytical techniques. This can be useful for applications such as medical diagnostics, biomedical research, environmental monitoring, food safety assurance and other uses.

In various embodiments, the present disclosure combines the ability to capture and isolate cells of interest and in addition separate the genomic DNA from the selected cells for analysis of the DNA and other cellular components from a large number of cells or even one selected cell. A microfluidic device of the present disclosure that performs cell and DNA capture can be usefully incorporated into a system for efficient, manual or automated, analysis. A schematic of one embodiment of such a system is shown schematically in FIG. 1, as discussed further herein.

In various embodiments, the present disclosure provides a technology that does not rely on DNA sequencing at all. For example, in certain embodiments, the devices, systems, and methods of the present disclosure can involve the use of fluorescence DNA probes specific for key TA-mutations to rapidly target and identify the presence or absence of TA-mutations. One goal of the present disclosure is to achieve such results within an hour using the micropillar-array based microfluidic device technology described herein. Thus, according to the present disclosure, the microfluidic device technology of the present disclosure can then be translated into a platform technology that doctors can operate without the additional need for sample transfer, lab technicians, or a separate facility.

Beyond just cancer, this same technology can be applied to the rapid detection and identification of any specific gene sequence or gene mutation from one or more selected cells. Applications can include, but are not limited to, pathogen identification in infectious diseases, identification of antibiotic resistant bacterial strains, food contamination testing for preventing or investigating foodborne illnesses, or even non-diseases related applications such as paternity testing.

Selective polymerase chain reaction or other selective DNA amplification processes can be used to detect specific gene sequences with high sensitivity. This would not require optical analysis or fluorescent detection of labels.

It is also possible to capture cellular DNA in the form of chromatin, consisting of genomic DNA with attached histones, and enable analysis of epigenetic histone modifications by detection of bound probes identifying different modifications.

Epigenetic modifications of DNA can be done by bisulfite sequencing of the DNA captured in the chip or by other standard methods.

As show in FIG. 1, the material to be extracted can be the genomic DNA, chromatin, or cell lysate other than the DNA. For example, by retaining the genomic DNA in the chip all other cell lysate material can be captured in chip output (feature 8 of FIG. 1) and a separate step the DNA can be extracted in a subsequent step and separately collected. This provides the possibility to collect and analyze the genomic DNA and separately collect the remaining cell lysate, containing proteins, lipids, RNA, mitochondrial DNA and other molecules from the same cell or cells. The off-chip analysis (box 9 in FIG. 1) can therefore be any of the available and developing methods of biochemical analysis such as mass spectrometry, chromatography, DNA sequencing, RNA sequencing, analysis by nucleic acid hybridization or other analytical methods.

Microfluidic Chip for On-Chip Analysis of Nucleic Acid Samples

In one aspect, the present disclosure relates to a microfluidic chip for on-chip detection of a presence or absence of a target nucleic acid region in an isolated nucleic acid sample. The microfluidic chip includes: (a) a nucleic acid entanglement array comprising a plurality of nucleic acid entanglement micropillars configured and arranged in a manner effective to physically entangle and maintain thereon an isolated nucleic acid sample; (b) the isolated nucleic acid sample immobilized in the nucleic acid entanglement array; and (c) at least one probe specific to a target nucleic acid region, said at least one probe being specifically bound to the target nucleic acid region and detectable when said isolated nucleic acid sample includes the target nucleic acid region, thereby enabling on-chip analysis of the presence or absence of the target nucleic acid region in the isolated nucleic acid sample.

In one embodiment, the isolated nucleic acid sample includes, without limitation, genomic DNA (gDNA), extra-chromosomal DNA, chromatin, plasmid DNA, a nucleic acid aptamer, an oligonucleotide, and/or a nucleic acid biomarker. In certain embodiments, the isolated nucleic acid sample can be in the form of single-stranded DNA, double-stranded DNA, or a combination of both single- and double-stranded DNA.

Various target nucleic acid regions are contemplated in accordance with the present disclosure. In one embodiment, the target nucleic acid region can include, without limitation, a gene, mutation, or nucleotide sequence from a eukaryotic cell. The eukaryotic cell can be from any organism, including, but not limited to any member of the Bacteria, Phage, Protista, Plantae, Fungi, and Animalia kingdoms.

In certain embodiments, the target nucleic acid region includes a gene, mutation, or nucleotide sequence from an animal. In particular embodiments, the target nucleic acid region can include, without limitation, a gene, mutation, or nucleotide sequence from a human or non-human animal. As used herein, a "non-human animal" includes any member of the animal kingdom that is not a human, including, without limitation, such animals as dogs, cats, horses, goats, pigs, cows, bison, chicken, fish, birds, and the like.

In certain embodiments, the target nucleic acid region includes a gene, mutation, or nucleotide sequence that is related to or that is a marker for the presence or risk of a disease or abnormal condition of a multicellular organism.

In certain embodiments, the disease or abnormal condition is a human disease including, without limitation, cancer, Down's syndrome, Huntington's disease, heart disease, thalassemia, cystic fibrosis, tay-sachs disease, sickle cell anemia, marfan syndrome, fragile X syndrome, hemochromatosis, and the like.

In certain embodiments, the disease or abnormal condition is a canine disease including, without limitation, hip dysplasia, urinary bladder stones, epilepsy, heart disease, degenerative myelopathy, brachycephalic syndrome, and the like.

In certain embodiments, the disease is cancer and the mutation is a therapeutically-actionable (TA) mutation.

In certain embodiments, the isolated nucleic acid sample is isolated from one or more cell.

In certain embodiments, the target nucleic acid region is specific for a pathogen, antibiotic resistant strain of bacteria, food contaminant, foodborne illness, paternity determination, DNA fingerprinting, individual identity, or the like.

In certain embodiments, the at least one probe includes, without limitation, a collection of multiple probes with each probe being specific to a unique (e.g., different) target nucleic acid region or to another probe which is specific to a unique target nucleic acid region.

In certain embodiments, the collection of multiple probes includes, without limitation, a panel of probes effective to produce a genetic profile for a disease or abnormal condition in a multicellular organism (e.g., a mammalian subject).

In certain embodiments, the probe is a fluorescence probe.

In certain embodiments, the probe can include, without limitation, molecular beacons, peptide nucleic acid probes, aptamers, protein probes, and the like.

Microfluidic System for On-Chip Analysis of Nucleic Acid Samples

In another aspect, the present disclosure relates to a microfluidic system for on-chip detection of the presence or absence of a target nucleic acid region in an isolated nucleic acid sample. The system includes: (a) an input controller component for introducing fluids, cells, reagents, and probes into the system under flow conditions; (b) a collection reservoir for collecting materials exported out of the system; (c) at least one microfluidic chip according to those described and contemplated herein, where the at least one microfluidic chip is detachably connected to the fluid controller by a fluidic input port and detachably connected to the collection reservoir by an output port; and (d) a detection component (e.g., optical system, camera, microscope, computer for image analysis) effective for on-chip detection of the presence or absence of the target nucleic acid region in the isolated nucleic acid sample immobilized on the at least one microfluidic chip.

As used herein, an "input controller component" includes any component suitable for controlling the flow of fluid into the microfluidic system, including, without limitation, for use of the microfluidic system for on-chip analysis of nucleic acid samples. An input controller component can include, for example, components such as a programmable fluid controller, a hydrodynamic pump, a mechanism for pressure driven force suitable for introducing and/or controller the introduction of fluids, cells, reagents, and/or probes into the microfluidic system under flow conditions. Suitable input controller components and related technology for use in the present disclosure can also be those as further described in PCT/US2017/033789 (WO 2017/205267-A1), PCT/US2017/033885 (WO 2017/205304-A1), U.S. Pat. Nos. 9,803,192, and/or 9,926,552, the disclosures of which are hereby incorporated by reference herein.

In certain embodiments, the microfluidic system further includes a multiplexed microfluidic flow directing system that functions to assist in directing flow of materials into the microfluidic system, through the microfluidic system, and out of the microfluidic system. The multiplexed microfluidic flow directing system includes a plurality of reconfigurable microfluidic layers that form a plurality of reconfigurable microfluidic channels. Suitable components and related technology for use in the microfluidic system and multiplexed microfluidic flow directing system of the present disclosure can also be those as further described in PCT/US2017/033789 (WO 2017/205267-A1), PCT/US2017/033885 (WO 2017/205304-A1), U.S. Pat. Nos. 9,803,192, and/or 9,926,552, the disclosures of which are hereby incorporated by reference herein.

In certain embodiments, the at least one microfluidic chip is functionally integrated with the multiplexed microfluidic flow directing system. In particular embodiment, the at least one microfluidic chip is integrated with the multiplexed microfluidic flow directing system in a manner so that flow of materials into the microfluidic system is directed into and through the at least one microfluidic chip before being exported from the microfluidic system.

In certain embodiments, the multiplexed microfluidic flow directing system is configured to receive and export one or more sample in a manual and/or automated fashion.

In certain embodiments, the multiplexed microfluidic flow directing system is configured to receive the one or more sample via one or more pipette.

In certain embodiments, the multiplexed microfluidic flow directing system is configured to assist in sorting materials for export from the microfluidic system for further collection, purification, and/or analysis, as described herein and/or as further described in PCT/US2017/033789 (WO 2017/205267-A1), PCT/US2017/033885 (WO 2017/205304-A1), U.S. Pat. Nos. 9,803,192, and/or 9,926,552, the disclosures of which are hereby incorporated by reference herein.

Method of On-Chip Analysis of Nucleic Acid Samples

In another aspect, the present disclosure relates to a method for on-chip detection of a presence or absence of a target nucleic acid region in an isolated nucleic acid sample. This method involves: (i) providing a microfluidic system as described or contemplated herein; and (ii) operating the microfluidic system in a manner sufficient to conduct on-chip detection of the presence or absence of a target nucleic acid region in an isolated nucleic acid sample.

In certain embodiments, the step of operating the microfluidic system involves: (i) introducing at least one cell of interest into the microfluidic system using the input controller component under conditions sufficient to: (a) capture the at least one cell of interest; (b) extract gDNA from the captured at least one cell of interest; and (c) isolate and immobilize the gDNA in the nucleic acid entanglement micropillars of the microfluidic chip; (ii) providing at least one probe specific to the target nucleic acid region and introducing the at least one probe into the microfluidic system using hydrodynamic flow and under conditions sufficient to allow the at least one probe to contact and specifically bind to the isolated and immobilized gDNA if the target nucleic acid region is present in the gDNA; and (iii) using the detection component for on-chip detection of the presence or absence of the target nucleic acid region in the isolated and immobilized gDNA.

In certain embodiments, the microfluidic system used in this method can further include a multiplexed microfluidic flow directing system having a plurality of reconfigurable microfluidic layers that form a plurality of reconfigurable microfluidic channels, where the multiplexed microfluidic flow directing system functions to assist in directing flow of materials into the microfluidic system, through the microfluidic system, and out of the microfluidic system. As used herein, the term "materials" includes anything flowed into the microfluidic system, including, for example, any fluid, composition, substance, cell, cell part, subcellular part, and the like.

In certain embodiments, the at least one microfluidic chip is functionally integrated with the multiplexed microfluidic flow directing system. In particular embodiment, the at least one microfluidic chip is integrated with the multiplexed microfluidic flow directing system in a manner so that flow of materials into the microfluidic system is directed into and through the at least one microfluidic chip before being exported from the microfluidic system.

In certain embodiments, the multiplexed microfluidic flow directing system is configured to receive and export one or more sample in a manual and/or automated fashion.

In certain embodiments, the multiplexed microfluidic flow directing system is configured to receive the one or more sample via one or more pipette.

In certain embodiments, the multiplexed microfluidic flow directing system is configured to assist in sorting materials for export from the microfluidic system for further collection, purification, and/or analysis, as described herein and/or as further described in PCT/US2017/033789 (WO 2017/205267-A1), PCT/US2017/033885 (WO 2017/205304-A1), U.S. Pat. Nos. 9,803,192, and/or 9,926,552, the disclosures of which are hereby incorporated by reference herein.

In one embodiment, the isolated nucleic acid sample includes, without limitation, genomic DNA (gDNA), extra-chromosomal DNA, chromatin, plasmid DNA, a nucleic acid aptamer, an oligonucleotide, and/or a nucleic acid biomarker. In certain embodiments, the isolated nucleic acid sample can be in the form of single-stranded DNA, double-stranded DNA, or a combination of both single- and double-stranded DNA.

Various target nucleic acid regions are contemplated in accordance with the present disclosure. In one embodiment, the target nucleic acid region can include, without limitation, a gene, mutation, or nucleotide sequence from a eukaryotic cell. The eukaryotic cell can be from any organism, including, but not limited to any member of the Bacteria, Phage, Protista, Plantae, Fungi, and Animalia kingdoms.

In certain embodiments, the target nucleic acid region includes a gene, mutation, or nucleotide sequence from an animal. In particular embodiments, the target nucleic acid region can include, without limitation, a gene, mutation, or nucleotide sequence from a human or non-human animal. As used herein, a "non-human animal" includes any member of the animal kingdom that is not a human, including, without limitation, such animals as dogs, cats, horses, goats, pigs, cows, bison, chicken, fish, birds, and the like.

In certain embodiments, the target nucleic acid region includes a gene, mutation, or nucleotide sequence that is related to or that is a marker for the presence or risk of a disease or abnormal condition of a multicellular organism.

In certain embodiments, the disease or abnormal condition is a human disease including, without limitation, cancer, Down's syndrome, Huntington's disease, heart disease, thalassemia, cystic fibrosis, tay-sachs disease, sickle cell anemia, marfan syndrome, fragile X syndrome, hemochromatosis, and the like.

In certain embodiments, the disease or abnormal condition is a canine disease including, without limitation, hip dysplasia, urinary bladder stones, epilepsy, heart disease, degenerative myelopathy, brachycephalic syndrome, and the like.

In certain embodiments, the disease is cancer and the mutation is a therapeutically-actionable (TA) mutation.

In certain embodiments, the isolated nucleic acid sample is isolated from one or more cell.

In certain embodiments, the target nucleic acid region is specific for a pathogen, antibiotic resistant strain of bacteria, food contaminant, foodborne illness, paternity determination, DNA fingerprinting, individual identity, or the like.

In certain embodiments, the at least one probe includes, without limitation, a collection of multiple probes with each probe being specific to a unique (e.g., different) target nucleic acid region or to another probe which is specific to a unique target nucleic acid region.

In certain embodiments, the collection of multiple probes includes, without limitation, a panel of probes effective to produce a genetic profile for a disease or abnormal condition in a multicellular organism (e.g., a mammalian subject).

In certain embodiments, the probe is a fluorescence probe.

In certain embodiments, the probe can include, without limitation, molecular beacons, peptide nucleic acid probes, aptamers, protein probes, and the like.

Turning to FIG. 1, there is shown a schematic of an embodiment illustrating the use of the microfluidic chip in a microfluidic system for performing the method for on-chip detection of the presence or absence of a target nucleic acid region in an isolated nucleic acid sample. As shown, the microfluidic system can include a cell-containing input 1 (e.g., blood), reagent reservoirs 2, a fluid controller manifold 3, detachable fluid connections 4, a chip manifold 6 containing microfluidic chip 7, a chip output collection component 8 (including for samples or waste), an optical system 10, a computer monitoring, control, and image analysis component 11, as well as optional integration with other analysis components 9 (e.g., DNA sequencing).

Integrated Microfluidic Cell Processing System

The present disclosure provides, inter alia, devices, systems, and methods for use in integrated microfluidic cell processing systems, as further described below. One feature of this technology is the use microfluidic and microchannel technologies in systems involving multiplexed analysis of cells and their contents. Furthermore, the microfluidic chip and a microfluidic system containing the microfluidic chip described herein can be included in the integrated microfluidic cell processing systems of the present disclosure. Further, in certain embodiments, the functions of the microfluidic chip of the present disclosure and/or the microfluidic chip itself can be include in the integrated microfluidic cell processing system.

In certain aspects, the present disclosure provides a system for rapidly analyzing many individual cells or many individual samples each with multiple cells. In certain embodiments, the present disclosure provides a system in the format of a microwell plate to facilitate integration with automated sample handling systems. In certain embodiments, the system has sample input and output connections with the spacing of standardized formats such as, but not limited to, those used in 96-well plates or 384-well plates. Sample introduction could use existing automated pipetting approaches and dispense material into microwell plates or other devices with standardized spacing. The output of the device will dispense material into tubing, microwell plates or other devices with arrays of receiving elements.

Various aspects, components, devices, protocols, systems, and embodiments for use in the integrated microfluidic cell processing systems of the present disclosure are further described in, for example, PCT/US2017/033789 (WO 2017/205267-A1) and PCT/US2017/033885 (WO 2017/205304-A1), the disclosures of which form an integral part of this disclosure, and which are hereby incorporated by reference herein in their entirety. More specifically, PCT/US2017/033789 (WO 2017/205267-A1) and PCT/US2017/033885 (WO 2017/205304-A1) describe various microfluidic devices that can be used for capturing one or more selected cells and separating genomic DNA of these cells from other cellular components for analysis. Therefore, the disclosures contained in PCT/US2017/033789 (WO 2017/205267-A1) and PCT/US2017/033885 (WO 2017/205304-A1) can be used with the devices, systems, and methods of the present disclosure.

The integrated microfluidic cell processing system of the present disclosure combines the ability to capture and isolate cells of interest in a microfluidic format and separate the genomic DNA from the selected cells from other cellular components. Individual microfluidic devices can do this from a large number of cells or even individual selected cell. In accordance with the integrated microfluidic cell processing system of the present disclosure, many of these types of microfluidic devices that perform cell and DNA capture can be incorporated in a multiplexed system for efficient, possibly automated, analysis. Schematic of embodiments of such multiplexed systems are shown schematically in FIGS. 3A-3D and FIGS. 4A-4D.

As shown in FIGS. 3A, 3B, 4A, and 4B, in certain embodiments, the integrated microfluidic cell processing system of the present disclosure can include microfluidic devices made, for example, by molding PDMS, can be incorporated as one or more intermediate layers (see item 5 in FIGS. 3A, 3B, 4A, and 4B) laminated into a more complex sample handling system. The construction of the microfluidic layer can use standard planar microfluidic fabrication processes, but in the present disclosure one or more planar microfluidic layers are coupled with reconfigurable layers (items 1 and 2 in FIGS. 3A, 3B, 4A, and 4B) that enable easily changing the function of the system. Each microfluidic component, for example, can also have more than one fluid input or output to enable a range of processes such as washing or separation of various cellular components. In certain embodiments, the system can include many independent devices each processing independent samples and delivering separate samples for collection and analysis.

Turning to FIGS. 3A-3D and FIGS. 4A-4D, there are shown different embodiments of the multiplexed microfluidic flow directing system according to the present disclosure. In the embodiment shown in FIGS. 3A-3D, the multiplexed microfluidic flow directing system does not include a microfluidic chip integrated into at least one layer of the multiplexed microfluidic flow directing system. In contrast, in the embodiment shown in FIGS. 4A-4D, the multiplexed microfluidic flow directing system does include a microfluidic chip integrated into at least one layer of the multiplexed microfluidic flow directing system. In certain embodiments, multiplexed microfluidic flow directing system of the present disclosure can include a combination of the features found in the systems shown in FIGS. 3A-3D and FIGS. 4A-4D. For example, in some embodiments, certain of the microfluidic channels can include the microfluidic chip (FIGS. 4A-4D), while other microfluidic channels on the same system can exclude the microfluidic chip (FIGS. 3A-3D).

Figure 3A:
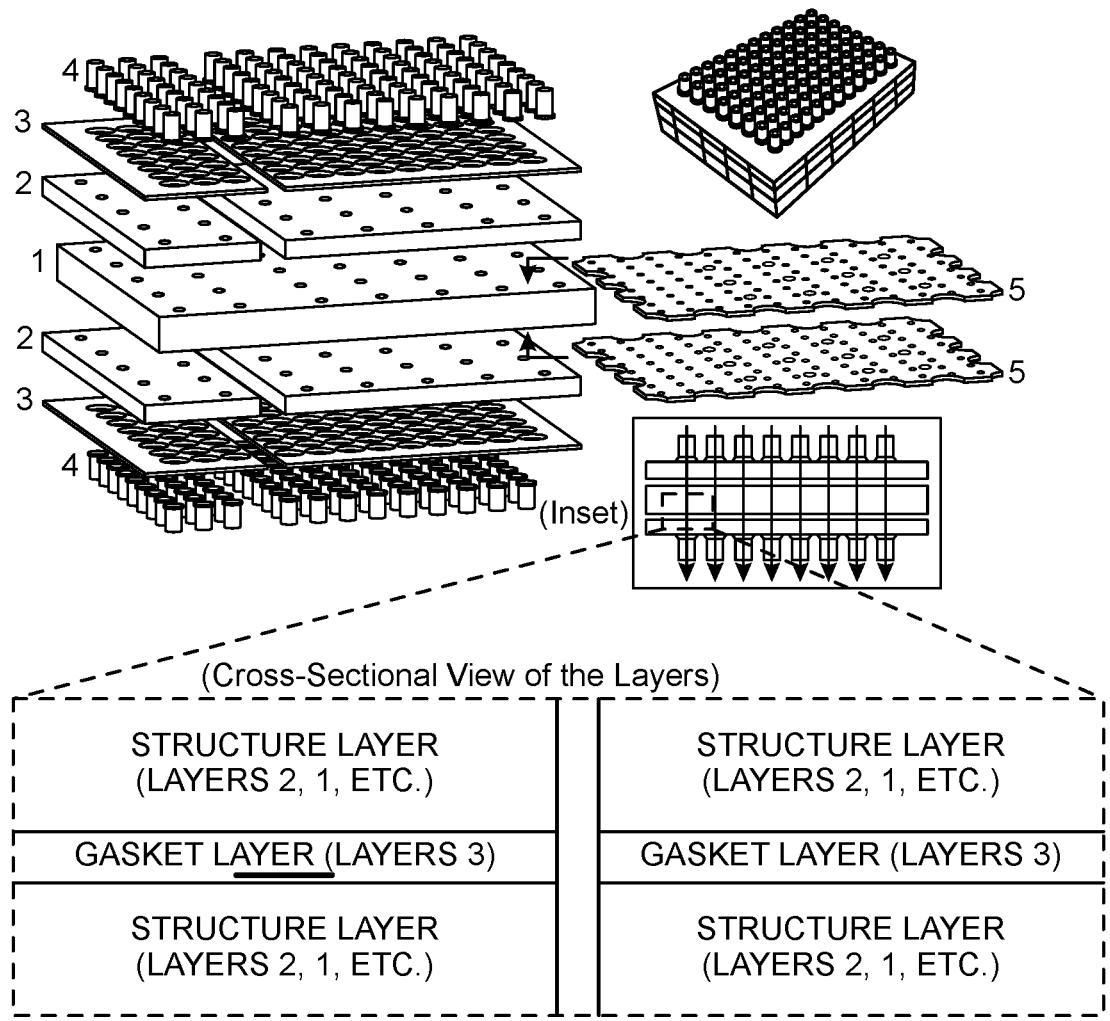
FIGS. 3A-3D illustrate various aspects of an embodiment of a multiplexed microfluidic flow directing system according to the present disclosure, which does not include a microfluidic chip integrated into at least one layer of the multiplexed microfluidic flow directing system.
Figure 3B:
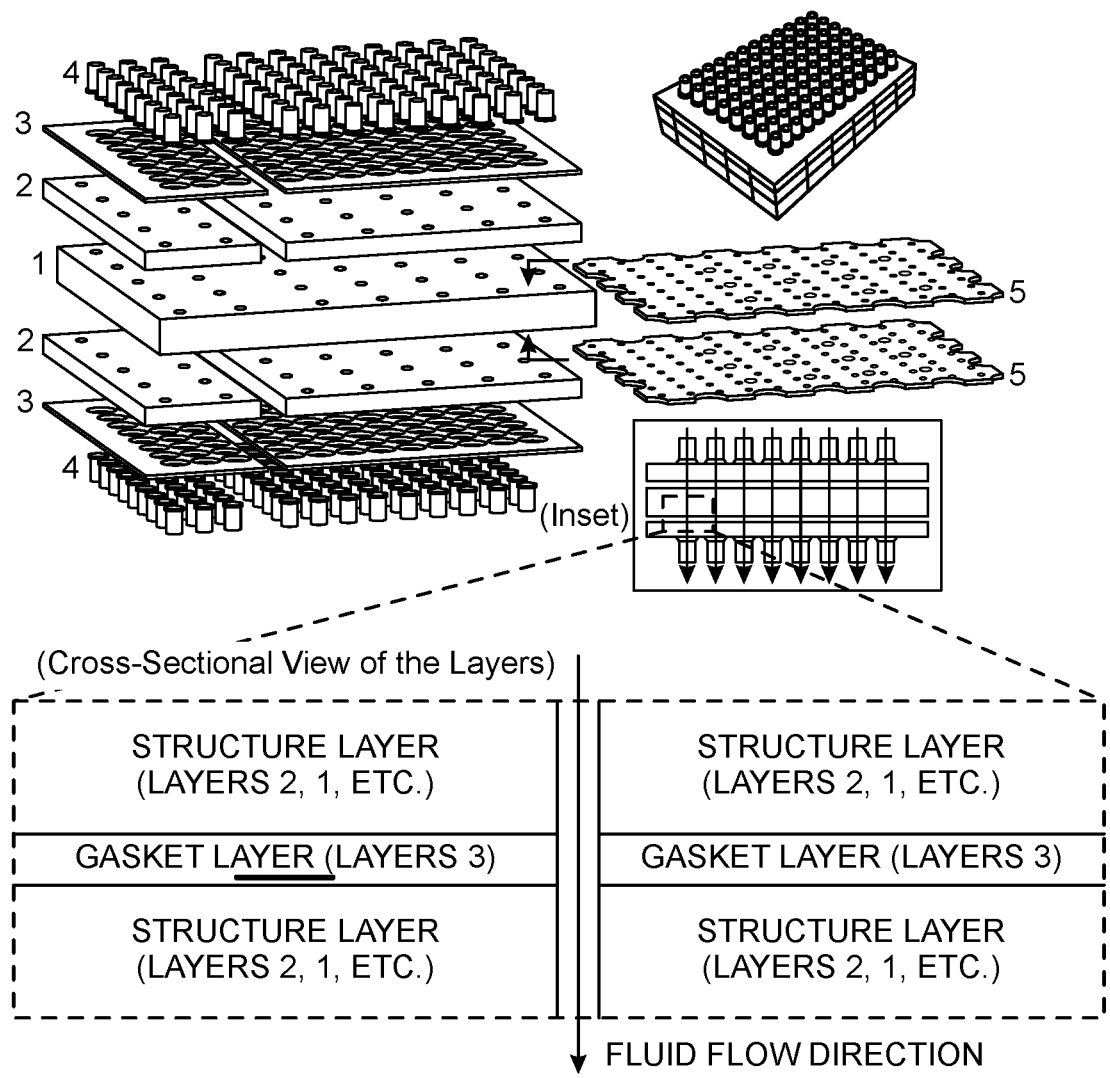
Figure 3C:
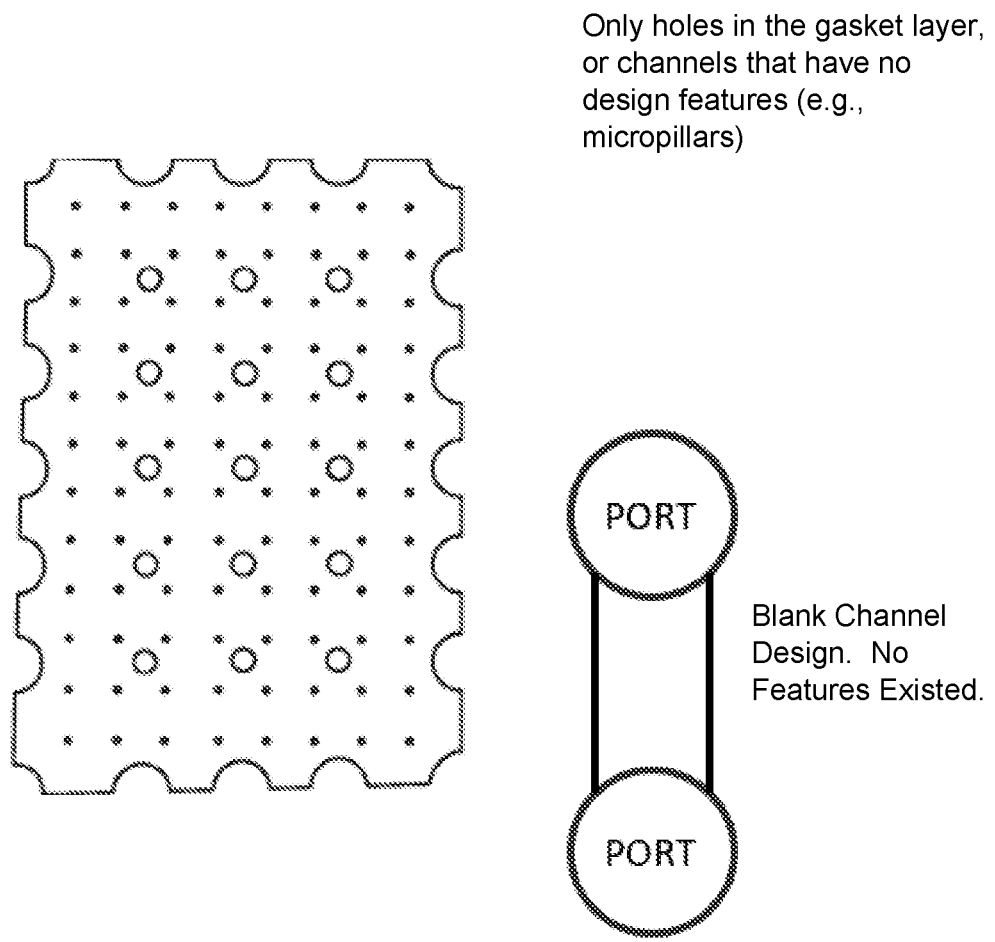
Figure 3D:
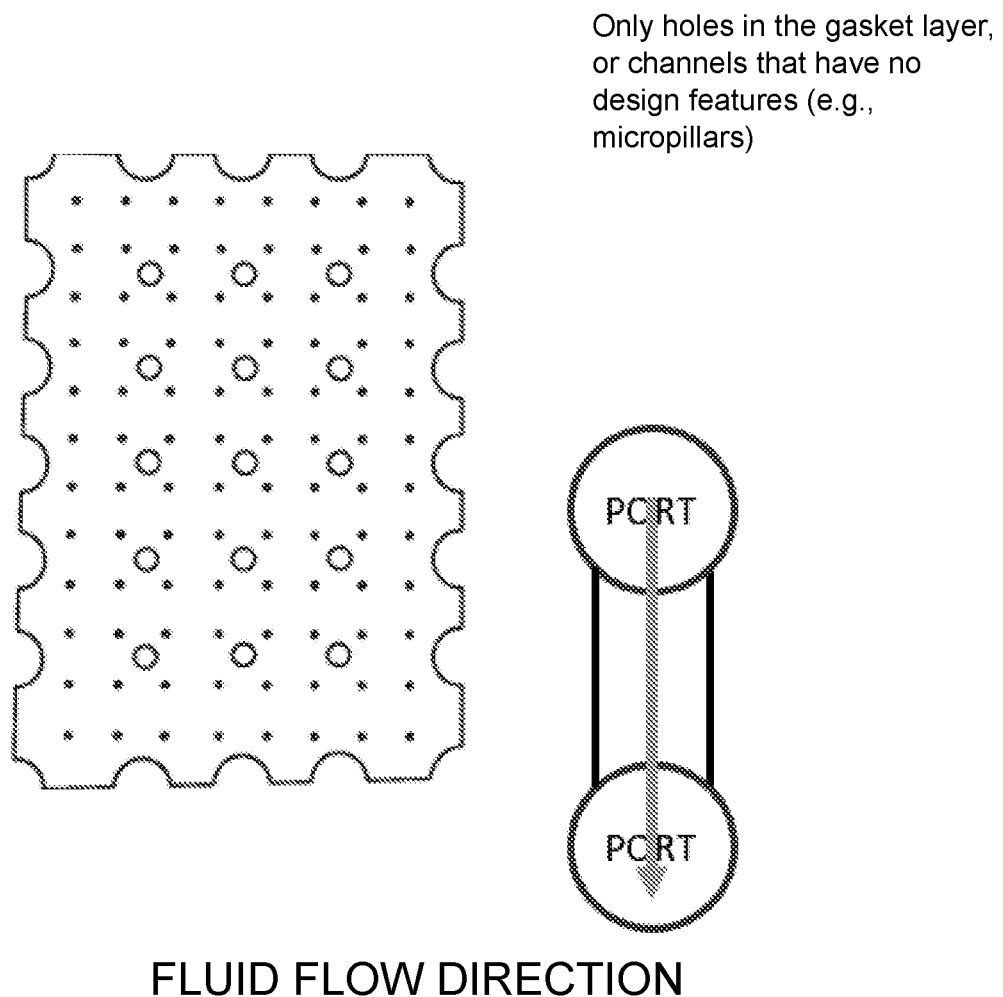
Figure 4A:
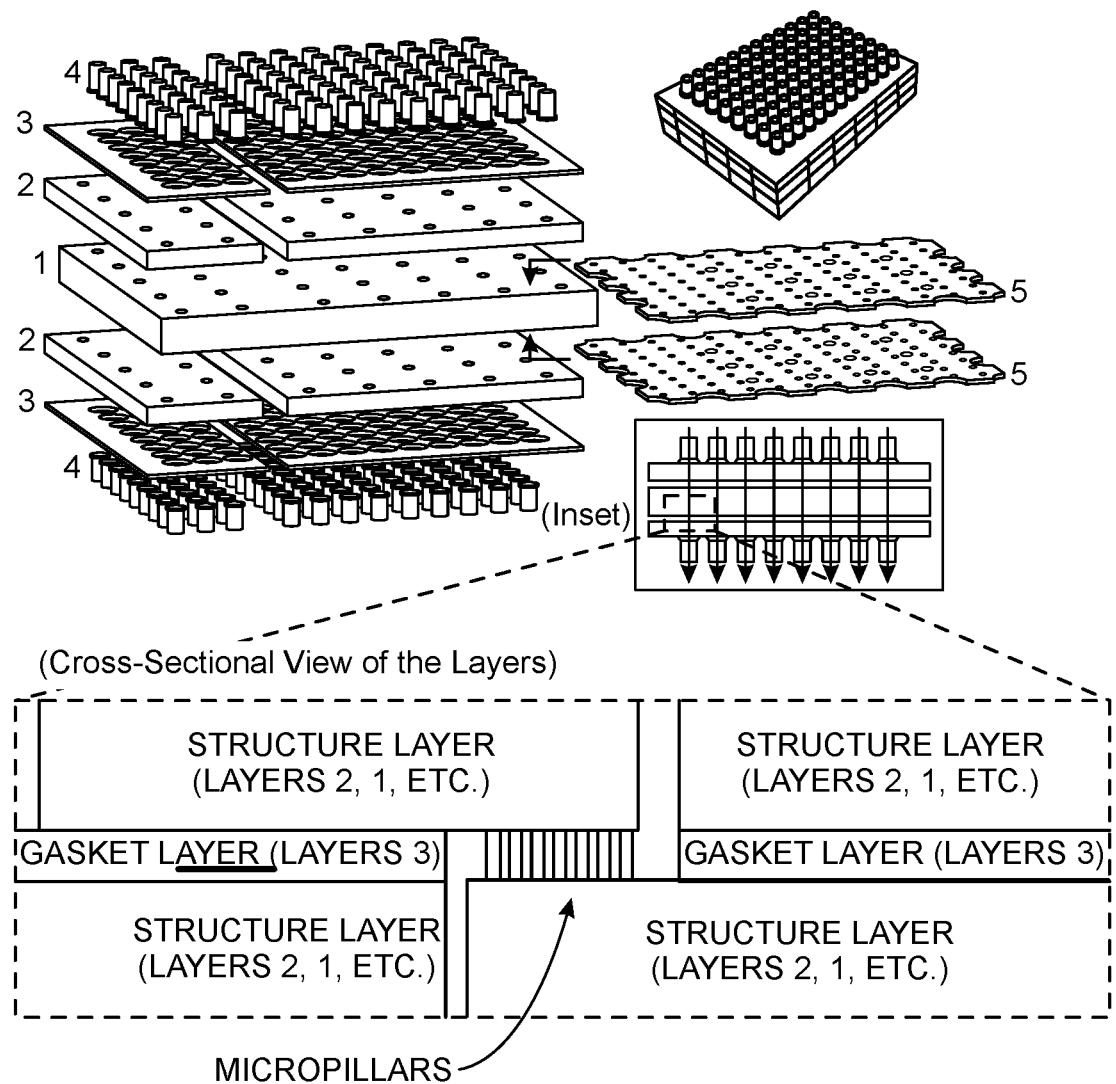
FIGS. 4A-4D illustrate various aspects of an embodiment of a multiplexed microfluidic flow directing system according to the present disclosure, which includes a microfluidic chip integrated (including micropillars) into at least one layer of the multiplexed microfluidic flow directing system.
Figure 4B:
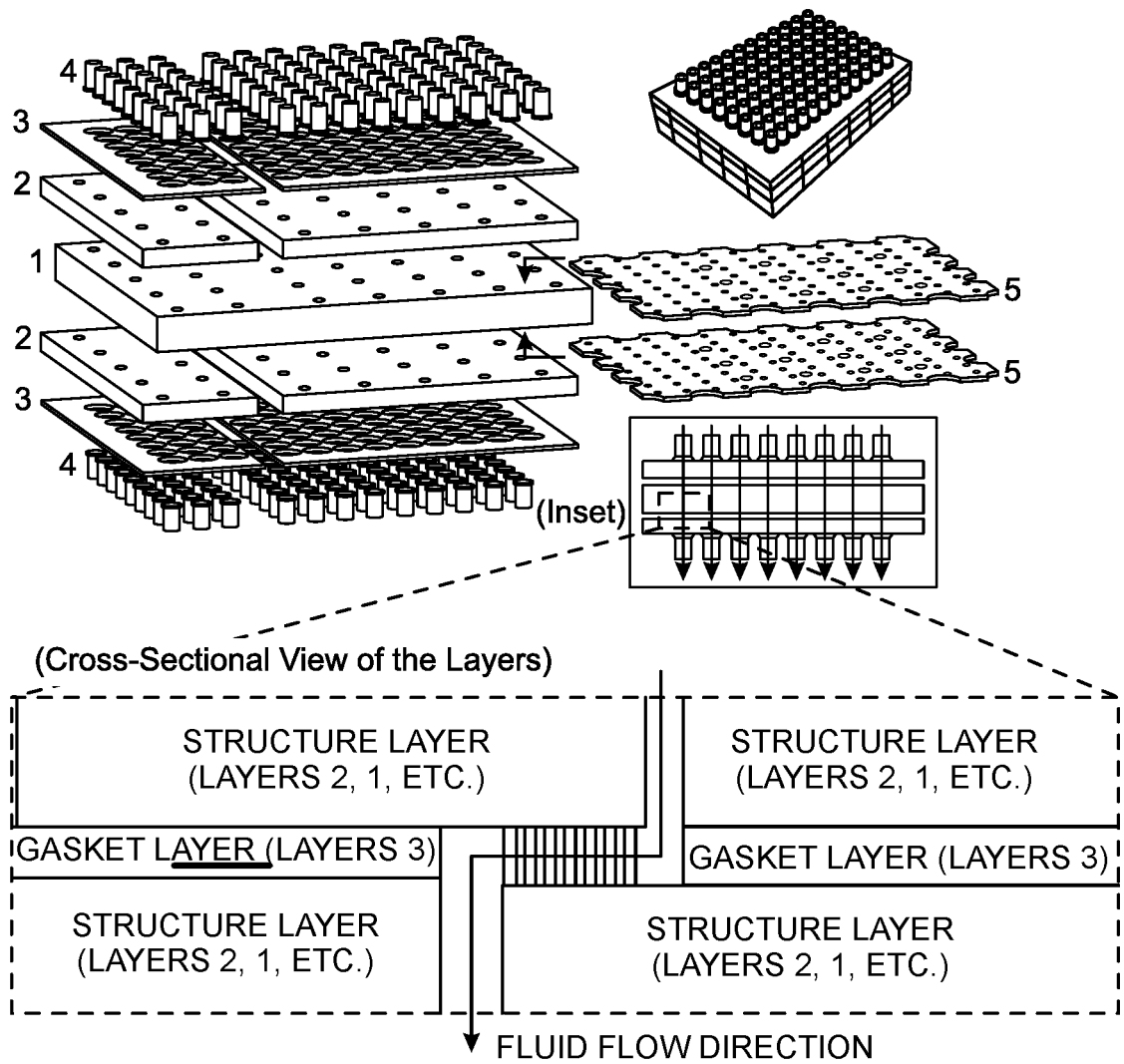
Figure 4C:
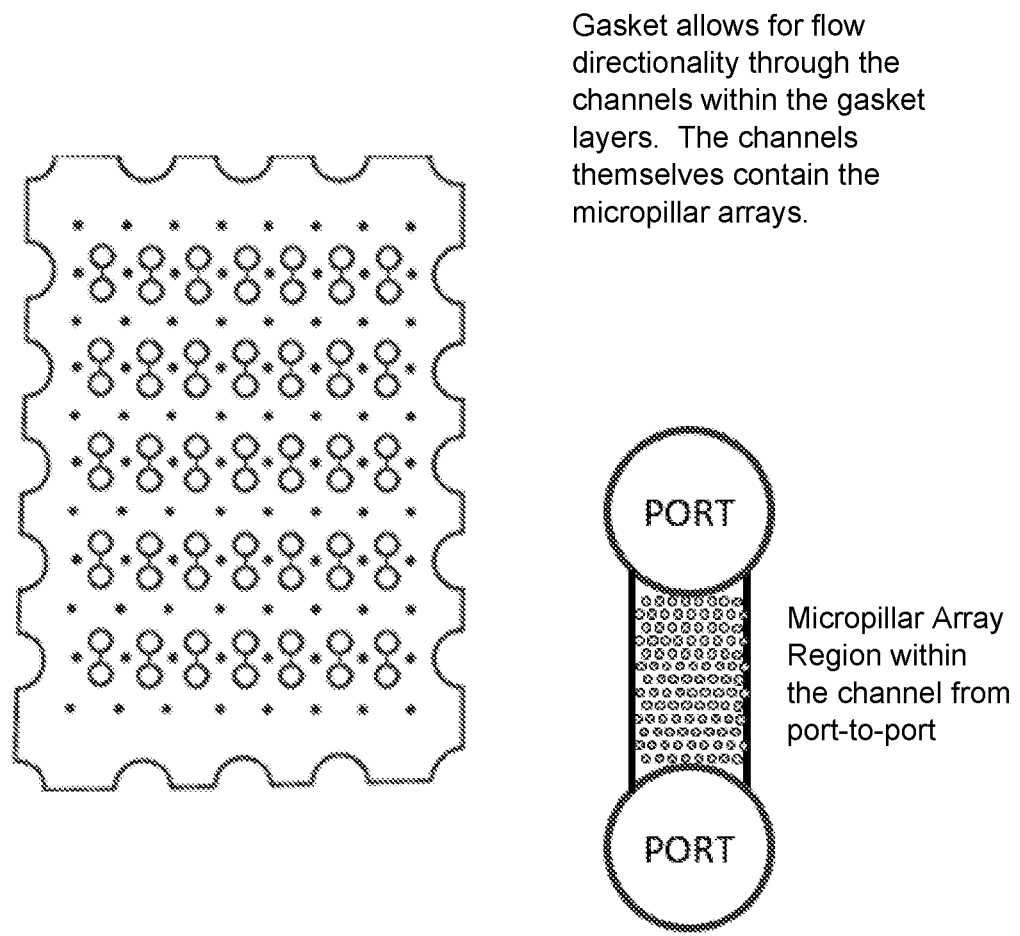
Figure 4D:
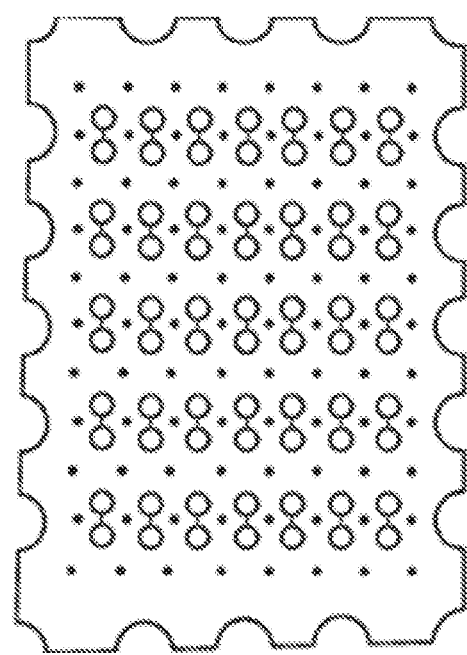
Figure 4D:
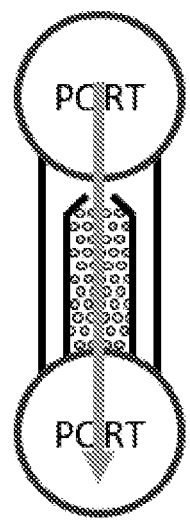

FIGS. 3A and 4A each illustrate an exploded view, a cross-sectional view, and a perspective view of a multiplexed microfluidic flow directing system of the present disclosure. FIGS. 3B and 4B each illustrate an exploded view, a cross-sectional view, and a perspective view of a multiplexed microfluidic flow directing system of the present disclosure, and further show the fluid flow direction through each respective system. Fluid flow in the system of FIG. 3B does not go through a microfluidic chip, while fluid flow in the system of FIG. 4B does go through a microfluidic chip before exiting the system. FIGS. 3C and 4C each illustrate a gasket layer and a close-up of a port and channel portion of their respective system. In the gasket layer and port/channel portion of FIG. 3C, there are only holes or channels that have no design features such as micropillars. In contrast, in the gasket layer and port/channel portion of FIG. 4C, the gasket and port/channel portions include micropillars and micropillar array regions within the channel from port-to-port, thereby allowing for flow directionality through the channels within the gasket layers. Further, the channels themselves contain the micropillar arrays that are used in the on-chip applications. FIGS. 3D and 4D each illustrate a gasket layer and a close-up of a port and channel portion of the system, and further show the fluid flow direction through the port and channel portion of each respective system. As shown in FIG. 3D, fluid does not flow through a micropillar array region. By way of contrast, as shown in FIG. 4D, fluid does flow through a micropillar array region. As described herein, embodiments of the multiplexed microfluidic flow directing system of the present disclosure can include gaskets and port/channel portions that have some port/channel portions that include micropillar array portions and others that do not.

Without being limiting, the multiplexed microfluidic flow directing systems of FIGS. 3A-3B and FIGS. 4A-4B can be configured in a manner similar to the layers of a microcolumn device (i.e., MEDUSA), including in the order of assembly. In certain embodiments, assembly of a multiplexed microfluidic flow directing system with or without any micropillar arrays (as shown in FIGS. 3A-3B and FIGS. 4A-4B) can be as follows: An exploded view of the customized device layers for configuring all 96 microcolumns to run in parallel. The flow path is shown in the lower boxed inset with no connections between microcolumns. The layers numbered 1 to 3 are the plastic layers: the middle layer (1) containing the microcolumns, the next outer two layers being the caps (2) and washers (3). The outermost layers (4) consist of inlet and outlet ports that are bonded to the final device. The two layers numbered (5) are silicone layers, which are bonded to the microcolumn layer (1) to hold porous frits against both sides of the microcolumns to retain affinity resin and to make liquid-tight seals across the entire device. A photograph of MEDUSA assembled in parallel is shown in the upper inset.

In accordance with the present disclosure, the integrated microfluidic cell processing system would facilitate the rapid analysis of many small samples that would be difficult to handle by standard bulk processes. It is contemplated that many (e.g., 384) of these processes will occur simultaneously in a multiplexed mode. In one embodiment, an example of a sequence of processes that could be accomplished in this system could include, without limitation, those steps listed below.

Step 1: Introduction of a sample such as blood, containing among other things a few rare cells of interest.

Step 2. Capture and retention of the cells of interest in the device whereby the cells have been identified by physical or chemical properties such as size, mechanical deformability, or biochemical compounds on the surface.

Step 3. Washing away of the unwanted components of the sample, e.g., other cells and liquids, and elution into an array of waste containers.

Step 4: Introduction of reagents to lyse the cells.

Step 5: Retention of the genomic DNA or chromatin on internal microstructures in the microfluidics such as an array of micron-scale pillars and collection of the other cellular components into an array of receiving vessels such as a microplate for subsequent analysis or processing. Unless further processed the collected material would include all of cellular contents other than the retained DNA or chromatin such as lipids, proteins, nucleic acids and small molecules. However, other in-system separations or processing are possible as discussed below.

Step 6: Analysis or amplification of the genomic DNA retained in the array by processes such as polymerase chain reaction or isothermal amplification processes, both of which can be done for selected genetic components or the entire genome. The DNA or chromatin can also be fluorescently labeled or have other compounds or enzymes bound to the retained DNA or chromatin. Bisulfite conversion or other chemical treatments are also possible.

Step 7: Release of the DNA, chromatin, modified DNA, or modified chromatin. This can be accomplished in a variety of ways such as chemical cleaving of the retained biopolymer or by changing the flow rate of the liquid in the microfluidic element to liberate the retained material from the internal microstructures. Collection of the released material in an array of receiving containers for further analysis or processing. As noted in Step 5, additional on system processes are possible through the use of appropriate buffers or flow conditions to isolate various cellular components.

As noted in Steps 5 and 7, the system can incorporate layers to perform other biochemical and physical processing of the samples. Layers 2 shown in FIGS. 3A, 3B, 4A, and 4B can include elements such as filters, chromatography columns, or media for treatment of samples before or after passage of material through the microfluidic layers. For examples, filters up stream of the microfluidic elements could remove unwanted components of the raw sample. Affinity chromatography material or selective binding media down-stream from the microfluidic layers could concentrate or isolate components of interest such as specific types of proteins, antibodies, RNA or DNA.

The parallel processing of cells in this system can facilitate richer analysis of small samples such as that from individual cells in a rapid and efficient manner. While difficult or impossible with currently available technology, with the system of the present disclosure, it will be possible to analyze many compounds of selected cells. This will enable, for example, revealing genetic sequence information, gene expression information and protein content of cells providing new insights into disease processes and possible avenues for treatment.

In one aspect, the present disclosure relates to an integrated microfluidic cell processing system. The integrated microfluidic cell processing system includes: a multiplexed microfluidic flow directing system having a plurality of reconfigurable microfluidic layers that form a plurality of reconfigurable microfluidic channels, where the multiplexed microfluidic flow directing system function to assist in directing flow of materials into, through, and out of the integrated cell processing system; and at least one microfluidic chip functionally integrated into at least one layer of the multiplexed microfluidic flow directing system, where the at least one microfluidic chip comprises a cell capture component and a nucleic acid entanglement component, and where the integrated microfluidic device operates under continuous flow conditions to process one or more cell.

In certain embodiments, the cell capture component includes a cell capture array having a plurality of cell capture micropillars, where the nucleic acid entanglement component includes a nucleic acid entanglement array having a plurality of nucleic acid entanglement micropillars.

In certain embodiments, the at least one microfluidic chip is functionally integrated with the multiplexed microfluidic flow directing system. In particular embodiment, the at least one microfluidic chip is integrated with the multiplexed microfluidic flow directing system in a manner so that flow of materials into the microfluidic system is directed into and through the at least one microfluidic chip before being exported from the microfluidic system.

In certain embodiments, the multiplexed microfluidic flow directing system is configured to receive and export one or more sample in a manual and/or automated fashion.

In certain embodiments, the multiplexed microfluidic flow directing system is configured to receive the one or more sample via one or more pipette.

In certain embodiments, the multiplexed microfluidic flow directing system is configured to assist in sorting materials for export from the microfluidic system for further collection, purification, and/or analysis, as described herein and/or as further described in PCT/US2017/033789 (WO 2017/205267-A1), PCT/US2017/033885 (WO 2017/205304-A1), U.S. Pat. Nos. 9,803,192, and/or 9,926,552, the disclosures of which are hereby incorporated by reference herein.

In certain embodiments, the multiplexed microfluidic flow directing system of the integrated microfluidic cell processing system includes a multiplexed device configured for conducting affinity chromatography in multiple microcolumns in parallel and/or in series.

Various embodiments of a multiplexed device of the present disclosure are programmable and reconfigurable, as described in more detail herein, and/or as further described in U.S. Pat. No. 9,803,192, the disclosures of which are hereby incorporated by reference herein.

In one embodiment, the multiplexed device of the present disclosure comprises: a microcolumn layer; a top capping layer; and a bottom capping layer. The microcolumn layer comprises a top surface, a bottom surface, and a plurality of substantially vertically aligned microcolumns for passing one or more sample liquids therethrough. The microcolumns extend from the top to the bottom surface of the microcolumn layer and optionally contain an affinity chromatography agent. The top capping layer is proximately disposed at the top surface of the microcolumn layer and comprises a patterned grid having at least one opening in fluid alignment with at least one microcolumn so as to allow a sample liquid to pass through the top capping layer and into the microcolumn. The bottom capping layer is proximately disposed at the bottom surface of the microcolumn layer and comprises either a parallel patterned grid for running multiple liquid samples through the microcolumns in a parallel manner or a series patterned grid for passing a single liquid sample through multiple serially connected microcolumns in a serial manner.

The microcolumn layer can be made of various materials suitable for use as described herein. Examples of suitable materials for the microcolumn layer include, without limitation, poly(methyl methacrylate) (PMMA), cyclic olefin copolymer, polyethylene, polypropylene, and polystyrene, or functional derivatives or variants thereof.

Similarly, the top capping layer and the bottom capping layer can be made of a material that includes, but is not limited to, poly(methyl methacrylate) (PMMA), cyclic olefin copolymer, polyethylene, polypropylene, and polystyrene, or functional derivatives or variants thereof.

The parallel patterned grid of the bottom capping layer comprises opening portions in fluid alignment with those microcolumns through which liquid samples are desired to pass in a parallel manner.

The series patterned grid of the bottom capping layer can further includes a bottom channel layer having a plurality of substantially horizontal channel portions, each forming a flow channel fluidly connecting adjacent microcolumns of the serially connected microcolumns through which the single liquid sample is desired to pass in a serial manner.

In one embodiment, the multiplexed device can further include a top channel layer disposed between the top capping layer and the top surface of the microcolumn layer. In such an embodiment, the top channel layer can include a plurality of substantially horizontal channel portions, each forming a flow channel fluidly connecting adjacent microcolumns of the serially connected microcolumns through which the single liquid sample is desired to pass in a serial manner.

In a particular embodiment, the top channel layer is patterned to work in fluid and serial connection with the plurality of horizontal channel portions of the bottom capping layer so as to pass the single liquid sample through the serially connected microcolumns in a serial manner.

The top channel layer can be made of any material suitable for allowing the top channel layer to function as described herein. Examples of suitable materials for use as the top channel layer include, without limitation, silicone, rubber, or any functional derivatives or variants thereof.

In one embodiment, the multiplexed device of the present disclosure further comprises a top port layer proximately disposed on the top capping layer. The top port layer comprises one or more input port, each in fluidic alignment with a corresponding microcolumn so as to effectuate introduction of a sample liquid into a desired microcolumn. In certain embodiments, the top port layer further comprises at least one outlet port for expelling a liquid sample from one of the microcolumns after it passes through a plurality of serially connected microcolumns in serial manner. As indicated, this sort of configuration is suitable for use in serial applications of the devise of the present disclosure.

In one embodiment, the multiplexed device of the present disclosure can further comprise a bottom port layer proximately disposed on the bottom capping layer. The bottom port layer comprises one or more outlet port, each in fluidic alignment with a corresponding microcolumn so as to effectuate expulsion of a liquid sample from a desired microcolumn.

The ports of the top port layer and bottom port layer can include, without limitation, NanoPorts™, connectors, tubing, or the like, or any structure suitable for performing the port function as described herein. A suitable material for use in making the ports can include, for example, a polymer, a thermoplastic polymer, polyether ether ketone (PEEK), or functional derivatives or variants thereof.

In one embodiment, the multiplexed device of the present disclosure further comprises a top frit gasket layer and/or a bottom frit gasket layer for aiding the containment of an affinity chromatography agent within the microcolumns. In such an embodiment, the top fit gasket layer is deposited between the top surface of the microcolumn layer and the top capping layer, and the bottom frit gasket layer is deposited between the bottom surface of the microcolumn layer and the bottom capping layer.

The top and bottom frit gasket layers can be made of various materials, particularly those materials suitable for use as gaskets, including, without limitation, materials such as silicone, rubber, plastic polymers (e.g., polychlorotrifluoroethylene), polytetrafluoroethylene (otherwise known as PTFE or Teflon), paper, metal, cork, felt, neoprene, nitrile rubber, and fiberglass, or functional derivatives or variants thereof.

In one embodiment, the multiplexed device of the present disclosure further comprises: a top port layer; an optional bottom port layer; a top washer layer; and/or a bottom washer layer. The top port layer is proximately disposed on the top capping layer, with the top port layer comprising one or more input port, each in fluidic alignment with a corresponding microcolumn so as to effectuate introduction of a sample liquid into a desired microcolumn. The optional bottom port layer is proximately disposed on the bottom capping layer and comprises one or more outlet port, each in fluidic alignment with a corresponding microcolumn so as to effectuate expulsion of a liquid sample from a desired microcolumn. The top washer layer and/or the bottom washer layer is provided for securing the ports of the top port layer and the optional bottom port layer in alignment with their corresponding microcolumns. The top washer layer is proximately deposited at the top capping layer and comprises a plurality of openings through which the ports of the top port layer protrude. The bottom washer layer is proximately deposited at the bottom capping layer and comprises a plurality of openings through which the ports of the optional bottom port layer protrude.

The top and bottom washer layers can be made of various materials that are suitable for use as washers for the ports. Examples of suitable materials for the washers include, without limitation, poly(methyl methacrylate) (PMMA), cyclic olefin copolymer, polyethylene, polypropylene, polystyrene, or functional derivatives and variants thereof.

As described herein, the microcolumn layer includes a plurality of substantially vertically aligned microcolumns for passing one or more sample liquids therethrough, particularly to effectuate affinity chromatography in the microcolumns. The microcolumns are generally channels that allow for a certain volume of liquid and/or affinity chromatography agents to reside in the microcolumn at a given moment.

The microcolumns can be of the same or varying volume capacity and dimension. In various embodiments, the microcolumns can have a volume capacity including, but not limited to, between about 0.5 µL and about 250 µL, between about 0.5 µL and about 225 µL, between about 0.5 µL and about 200 µL, between about 0.5 µL and about 175 µL, between about 0.5 µL and about 150 µL, between about 0.5 µL and 125 about µL, between about 0.5 µL and about 100 µL, between about 0.5 µL and about 90 µL, between about 0.5 µL and about 80 µL, between about 0.5 µL and about 70 µL, between about 0.5 µL and about 60 µL, between about 0.5 µL and about 50 µL, between about 0.5 µL and about 40 µL, between about 0.5 µL and about 35 µL, between about 0.5 µL and about 30 µL, between about 0.5 µL and about 25 µL, between about 0.5 µL and about 20 µL, between about 0.5 µL and about 15 µL, between about 0.5 µL and about 10 µL, between about 0.5 µL and about 5 µL, between about 0.5 µL and about 2.5 µL, between about 0.5 µL and about µL 2.0, between about 0.5 µL and about 1.5 µL, or between about 0.5 µL and about 1.0 µL.

As described herein, the microcolumns can optionally contain an affinity chromatography agent. Suitable affinity chromatography agents refer to any agent that is effective in aiding the affinity chromatography function of the microcolumn. Without intending to be limiting, examples of suitable affinity chromatography agents for the present disclosure can include, without limitation, a resin, a modified resin, microbeads, and the like.

In one embodiment, the affinity chromatography agent comprises an immobilized target molecule. In a particular embodiment, the immobilized target molecule is labeled. In certain embodiments, the immobilized target molecule can include, without limitation, a whole cell, a virus, a virus particle, a protein, a modified protein, a polypeptide, a modified polypeptide, an RNA molecule, a DNA molecule, a modified DNA molecule, a polysaccharide, an amino acid, an antibiotic, a pharmaceutical agent, an organic non-pharmaceutical agent, a macromolecular complex, a carbohydrate, a lipid, a small molecule, a chemical compound, a mixture of lysed cells, or a mixture of purified, partially purified, or non-purified protein.

In certain embodiments, the immobilized target molecule is provided from a mixture of lysed cells, a mixture of purified, partially purified, or non-purified protein.

As described herein, the multiplexed device of the present disclosure is useful for conducting affinity chromatography in multiple microcolumns, either in parallel and/or in series. As used herein, the term "affinity chromatography" is meant to cover all affinity chromatography techniques that can take place in a microcolumn, as described herein. For example, as used herein, affinity chromatography can involve, without limitation, anion exchange technology, group exclusions, immobilized-metal affinity chromatography (IMAC), fusion tag protein purification, pull-down assays, and/or immunoprecipitations.

In accordance with the device of the present disclosure, the one or more liquid sample can comprise one or more test agent for running through at least one of the microcolumns to determine its affinity or lack of affinity to the affinity chromatography agent. The test agent can include, without limitation, an aptamer, a protein, a protein complex, a modified protein, a polypeptide, a modified polypeptide, an RNA molecule, a DNA molecule, a modified DNA molecule, a drug, as well as any other molecules or ligands of interest.

In one embodiment of the integrated microfluidic cell processing system of the present disclosure, the microfluidic chip is configured for on-chip detection of a presence or absence of a target nucleic acid region in an isolated nucleic acid sample. Suitable microfluidic chips include: (a) a nucleic acid entanglement array comprising a plurality of nucleic acid entanglement micropillars configured and arranged in a manner effective to physically entangle and maintain thereon an isolated nucleic acid sample; (b) the isolated nucleic acid sample immobilized in the nucleic acid entanglement array; and (c) at least one probe specific to a target nucleic acid region, said at least one probe being specifically bound to the target nucleic acid region and detectable when said isolated nucleic acid sample includes the target nucleic acid region, thereby enabling on-chip analysis of the presence or absence of the target nucleic acid region in the isolated nucleic acid sample.

In one embodiment, the isolated nucleic acid sample includes, without limitation, genomic DNA (gDNA), extra-chromosomal DNA, chromatin, plasmid DNA, a nucleic acid aptamer, an oligonucleotide, and/or a nucleic acid biomarker. In certain embodiments, the isolated nucleic acid sample can be in the form of single-stranded DNA, double-stranded DNA, or a combination of both single- and double-stranded DNA.

Various target nucleic acid regions are contemplated in accordance with the present disclosure. In one embodiment, the target nucleic acid region can include, without limitation, a gene, mutation, or nucleotide sequence from a eukaryotic cell. The eukaryotic cell can be from any organism, including, but not limited to any member of the Bacteria, Phage, Protista, Plantae, Fungi, and Animalia kingdoms.

In certain embodiments, the target nucleic acid region includes a gene, mutation, or nucleotide sequence from an animal. In particular embodiments, the target nucleic acid region can include, without limitation, a gene, mutation, or nucleotide sequence from a human or non-human animal. As used herein, a "non-human animal" includes any member of the animal kingdom that is not a human, including, without limitation, such animals as dogs, cats, horses, goats, pigs, cows, bison, chicken, fish, birds, and the like.

In certain embodiments, the target nucleic acid region includes a gene, mutation, or nucleotide sequence that is related to or that is a marker for the presence or risk of a disease or abnormal condition of a multicellular organism.

In certain embodiments, the disease or abnormal condition is a human disease including, without limitation, cancer, Down's syndrome, Huntington's disease, heart disease, thalassemia, cystic fibrosis, tay-sachs disease, sickle cell anemia, marfan syndrome, fragile X syndrome, hemochromatosis, and the like.

In certain embodiments, the disease or abnormal condition is a canine disease including, without limitation, hip dysplasia, urinary bladder stones, epilepsy, heart disease, degenerative myelopathy, brachycephalic syndrome, and the like.

In certain embodiments, the disease is cancer and the mutation is a therapeutically-actionable (TA) mutation.

In certain embodiments, the isolated nucleic acid sample is isolated from one or more cell.

In certain embodiments, the target nucleic acid region is specific for a pathogen, antibiotic resistant strain of bacteria, food contaminant, foodborne illness, paternity determination, DNA fingerprinting, individual identity, or the like.

In certain embodiments, the at least one probe includes, without limitation, a collection of multiple probes with each probe being specific to a unique (e.g., different) target nucleic acid region or to another probe which is specific to a unique target nucleic acid region.

In certain embodiments, the collection of multiple probes includes, without limitation, a panel of probes effective to produce a genetic profile for a disease or abnormal condition in a multicellular organism (e.g., a mammalian subject).

In certain embodiments, the probe is a fluorescence probe.

In certain embodiments, the probe can include, without limitation, molecular beacons, peptide nucleic acid probes, aptamers, protein probes, and the like.

In certain embodiments, the integrated microfluidic cell processing system is suitable for collecting one or more liquid sample from an affinity chromatography microcolumn device, where the integrated microfluidic cell processing system further includes: (i) a liquid flow mechanism for moving a liquid sample into, through, and out of a microcolumn contained in the device; and (ii) a liquid collection apparatus comprising well portions for collecting liquid samples from the microcolumns, where each well portion is aligned with a single corresponding microcolumn for collection of the liquid sample therefrom. In an alternative embodiment, the liquid collection apparatus can comprise other structures that can function to collect liquid samples from each microcolumn in an organized manner, without the liquid collection apparatus including well portions. For example, instead, the well portions can be replaced with a tube or other sort of conduit that is in fluid alignment with a particular microcolumn so as to collect the liquid sample from that particular microcolumn.

The liquid flow mechanism can be any apparatus or technology suitable for causing the liquid samples to enter the desired microcolumns in a manner sufficient to conduct the affinity chromatography in the microcolumns. The liquid flow mechanism can be also be any apparatus or technology suitable for causing the liquid samples to enter the desired microcolumns in a manner sufficient to conduct the affinity chromatography in the microcolumns, as well as to for causing the liquid sample to exit the microcolumns. By exiting the microcolumns, the liquid samples that have undergone affinity chromatography in the microcolumns can then be collected for further analyses in accordance with the present disclosure. In a particular embodiment, the liquid flow mechanism is programmable to move the liquid samples through the microcolumns at a desired flow rate, at a desired volume, for a desired amount of time, and/or for a desired time interval.

Suitable liquid flow mechanisms in accordance with the present disclosure can include, without limitation, a pump for either pushing or pulling the liquid sample through one or more of the microcolumns. In a particular embodiment, the pump controls flow rate of the liquid samples through the microcolumns.

In accordance with the system described herein, the liquid collection apparatus can be any apparatus suitable for collecting the liquid samples once they exit the microcolumns. In a particular embodiment the liquid collection apparatus can include, without limitation, a microplate having a plurality of wells for collecting liquid samples from the microcolumns. Suitable microplates can include any plate that includes one or more well that can capture and hold liquid samples that exit from the microcolumns of the device of the present disclosure. In particular embodiments, the microplate is a standard microwell plate that includes the standard number and size of wells. Examples of the number of wells in a suitable microplate can include, without limitation, 6, 12, 24, 48, 96, 384, 1536, 3456, and 9600 wells.

Method for Cell Analysis Using an Integrated Microfluidic Cell Processing System In another aspect, the present disclosure relates to a method of collecting one or more liquid sample from an affinity chromatography microcolumn for further analysis. This method involves: providing an integrated microfluidic cell processing system described and/or contemplated herein; running one or more liquid sample through the microcolumns of the device of the system either in a parallel manner or a serial manner under conditions effective to allow a test agent contained in the liquid sample to bind specifically to a target molecule contained in the microcolumn of the device; and recovering from each microcolumn the test agent or test agents that bind specifically to the respective target molecules of each microcolumn device, the recovering taking place in the liquid collection apparatus.

In one embodiment of this method, the recovering step comprises the steps of: washing unbound and weakly bound test agents from each microcolumn; and eluting the test agents that specifically bind to the target molecules of each microcolumn.

In accordance with one embodiment of this method, the recovered test agents that specifically bind to the target molecules are nucleic acid aptamers comprising RNA aptamers. In such an embodiment, the method can further comprise performing reverse transcription amplification of the selected aptamer population.

In accordance with one embodiment of this method, the method can further comprise purifying and sequencing the amplified aptamer population.

In accordance with another embodiment of this method, the recovering, performing reverse transcription amplification, purifying, and/or sequencing steps are performed in one or more separate fluidic devices coupled in fluidic communication with the microcolumn devices of the present disclosure. Such separate fluidic devices are known in the relevant art by those of ordinary skill in the art.

In accordance with one embodiment of this method, each of the running and recovering steps is automated.

In accordance with another embodiment of this method, the liquid samples collected from the microcolumns are further used in analytical processes. Any analytical process suitable for use with microcolumn affinity chromatography is contemplated by the present disclosure. In certain embodiments, the analytical processes can involve, without limitation, high throughput processes, quantitative polymerase chain reaction (qPCR), UV-Visual absorption spectroscopy, fluorescence spectroscopy, nucleic acid sequencing (e.g, DNA sequencing), and mass spectrometry.

Combination of the Present Disclosure with Existing Technologies

Various aspects, components, devices, protocols, systems, and embodiments for use in the devices, systems, and methods for on-chip analysis of nucleic acids and in cell processing systems of the present disclosure are further described in, but not limited to, the following: PCT/US2017/033789 (WO 2017/205267-A1), entitled "Multifunctional Microfluidic Device for Capturing Target Cells and Analyzing Genomic DNA Isolated from the Target Cells While Under Flow Conditions"; PCT/US2017/033885 (WO 2017/205304-A1), entitled "Single Cell Whole Genome Amplification Via Micropillar Arrays Under Flow Conditions"; U.S. Pat. No. 9,803,192 (US2015/0166987-A1), entitled "Programmable and Reconfigurable Microcolumn Affinity Chromatography Device, System, and Methods of Use Thereof"; and U.S. Pat. No. 9,926,552, entitled "Microfluidic Device for Extracting, Isolating, and Analyzing DNA from Cells," the disclosures of which are hereby incorporated herein by reference.

More specifically, PCT/US2017/033789 (WO 2017/205267-A1), PCT/US2017/033885 (WO 2017/205304-A1), U.S. Pat. Nos. 9,803,192, and 9,926,552 describe various microfluidic devices or technologies that can be used for capturing one or more selected cells and separating genomic DNA of these cells from other cellular components for analysis.

The devices described in PCT/US2017/033789 (WO 2017/205267-A1) and PCT/US2017/033885 (WO 2017/205304-A1) utilize microfluidic devices containing microstructures to capture selected cells by size or affinity binding. By lysing the captured cells the genomic DNA can be immobilized in the device and separated from the other components of the lysed cells.

EXAMPLES

The following examples are intended to illustrate particular embodiments of the present disclosure, but are by no means intended to limit the scope of the present disclosure.

Example 1

Device, System, and Methods for Efficient Fluorescent Analysis of DNA from Selected Cells Current experiments are being developed and run to demonstrate the potential of using fluorescence probes by first verifying the specificity to which we can target DNA sequences. Preliminary results are outlined herein.

Similar to the technology described in PCT/US2017/033885, micropillar arrays are used to extract and retain genomic DNA (gDNA) from the target cells. In PCT/US2017/033885, the gDNA immobilized by the pillars are held in the microchannel as DNA amplification reagents are flowed into the channel and amplified DNA product is collected in an output port.

In accordance with the devices, systems, and methods of the present disclosure, here, we use a similar process for the initial cell trapping and DNA extraction, but instead of flowing in amplification reagents to the immobilized DNA we instead flow in commercially available DNA fluorescence probes that are target-sequence specific. FIG. 1 shows an overview for one embodiment of a system within which the technology would function. Similar to the system described in PCT/US2017/033885, flow is controlled from either a hydrodynamic pump or a pressure driven force. Reagents are loaded onto the microfluidic chip device containing a region of micropillar arrays upon which cells are immobilized, lysed, and the gDNA is captured. The fluorescence hybridization processes would all then happen on-chip while being observable via a microscope. Processing and analyzing the fluorescence data can then be either performed by hand, or automated with computer using programmable software.

Cells from either a laboratory or patient sample can be loaded into reservoirs that sync to the system. A fluid controller which can be programmed and automated loads the cells into a disposable microfluidic chip sitting within the chip manifold. While on the chip manifold, fluorescent probes can be hybridized to the gDNA that has been extracted from the cells. The gDNA treated with fluorescent probes can then be imaged using a camera and analyzed for the presence or absence of the target genetic sequence.

In certain experiments, our first step was to demonstrate that we can achieve a certain level of specificity with these probes, so we used fluorescence probes specific for a sequence present in human chromosome 17. In testing this probe with human cancer cell lines, we were able to yield a fluorescence signal whereas when this same process was repeated on mouse cells, the probe did not bind to the extracted DNA.

Therefore, we know that fluorescence probes can be used on purified gDNA immobilized on micropillars under a constant flow and still retain the specificity to the targeted DNA sequence. This is a novel process and this is an improvement on conventional fluorescence DNA probe methodologies. Conventionally, intact cells are spread onto a glass slide and must then be permeabilized before the probes can diffuse into the cells overnight in a 16+ hour incubation step. The technology of the present disclosure is superior to this conventional method at least by: (i) extracting the gDNA thereby eliminating the need for cell permeabilization, and then (ii) using hydrodynamic flow through our microchannel rather than relying on diffusion to carry the fluorescent probes to the gDNA itself. In experiments using the technology of the present disclosure, we have achieved the fluorescence identification on the order of a few hours, rather than needing overnight incubation. An object of the present disclosure is to further optimize the processes and buffers to reduce the probe hybridization to under an hour.

Figure 2A:
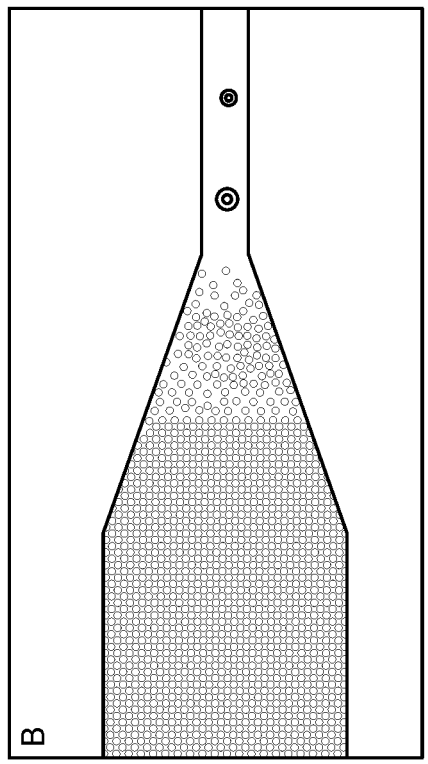
FIGS. 2A and 2B are micrographs illustrating one embodiment of a micropillar array for use in the microfluidic system and microfluidic chip of the present disclosure. The figures illustrate human chromosome-17-specific control fluorescence probe on DNA.
Figure 2B:
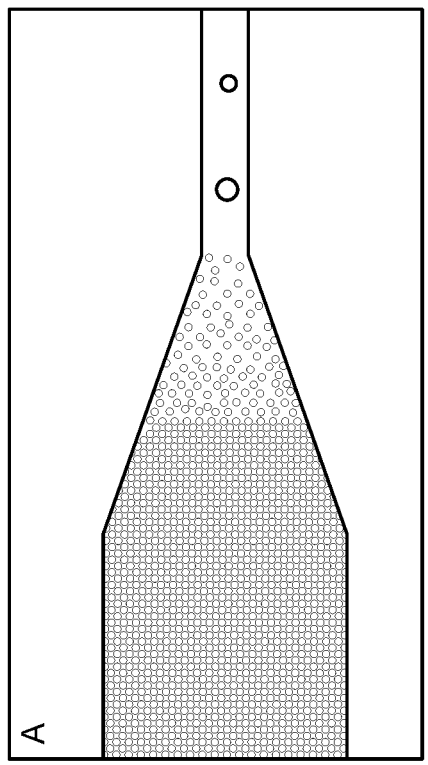

An example of the use of the above described process of the present disclosure on a micropillar device can be seen in FIGS. 2A and 2B, which illustrates human chromosome 17 specific control fluorescence probe on DNA.

In FIGS. 2A-2B, gDNA has already been extracted and immobilized onto the micropillars from (FIG. 2A) mouse cells (3T3 cell line) and (FIG. 2B) human cancer cells (HeLa cell line). Human chromosome 17 probes are then flowed into the device (direction of flow is from right-to-left) from the input port to the microfluidic device. After 2-3 hours, the probes have fluorescently binded to the human DNA in FIG. 2B, whereas it remains unbound to the mouse DNA. This suggests that the probe can be used in a specific manner that can target a selected sequence.

By using specific fluorescent DNA probes to target known TA-mutations on gDNA extracted from cancer cells derived from a cancer patient, this technology can be applied as a diagnostic for important cancer mutations in clinical settings. A panel of multiple fluorescent probes can be used on a single set of extracted gDNA on our chip-device either simultaneously or sequentially to provide a profile of cancer mutations which can give physicians a more informed treatment response.

Illustrative embodiments of the processes, methods, and products of the present disclosure are described herein. It should be understood, however, that the description herein of the specific embodiments is not intended to limit the present disclosure to the particular forms disclosed but, on the contrary, the intention is to cover all modifications, equivalents, and alternatives falling within the spirit and scope of the invention by the appended claims. Thus, although the present invention has been described for the purpose of illustration, it is understood that such detail is solely for that purpose and variations can be made by those skilled in the art without departing from the spirit and scope of the invention which is defined by the following claims.

What is claimed is:

1. An integrated microfluidic cell processing system comprising:
   a flow directing system comprising a plurality of reconfigurable microfluidic layers that include:
      an affinity microcolumn layer comprising a plurality of substantially vertical microcolumns passing therethrough and containing an affinity chromatography agent; and
      at least one microfluidic chip functionally integrated into a layer below the affinity microcolumn layer, wherein said at least one microfluidic chip comprises a cell capture component and a nucleic acid entanglement component,
   wherein the system operates under continuous flow conditions to process one or more cell.

2. The integrated microfluidic cell processing system according to claim 1, wherein said cell capture component comprises a cell capture array comprising a plurality of cell capture micropillars, and wherein said nucleic acid entanglement component comprises a nucleic acid entanglement array comprising a plurality of nucleic acid entanglement micropillars.

3. The integrated microfluidic cell processing system according to claim 1, wherein the at least one microfluidic chip is integrated with the flow directing system in a manner so that flow of materials into the flow directing system is directed into and through the at least one microfluidic chip before being exported from the flow directing system, and wherein the flow directing system is configured to: receive and export one or more sample in manual and/or automated fashion; and/or assist in sorting materials for export from the microfluidic system for further collection, purification, and/or analysis.

4. The integrated microfluidic cell processing system according to claim 1, further comprising:
   a top capping layer proximately disposed at a top surface of the affinity microcolumn layer and comprising a patterned grid having at least one opening in fluid alignment with at least one microcolumn so as to allow a sample liquid to pass through the top capping layer and into the at least one microcolumn;
   a bottom capping layer beneath a bottom surface of the affinity microcolumn layer and comprising a parallel patterned grid of openings in fluid alignment with the microcolumns; and
   a bottom frit gasket layer deposited between the bottom surface of the affinity microcolumn layer and the bottom capping layer for aiding the containment of the affinity chromatography agent.

5. The integrated microfluidic cell processing system according to claim 4 further comprising:
   a top channel layer disposed between the top capping layer and the top surface of the microcolumn layer, wherein the top channel layer comprises a plurality of substantially horizontal channel portions each forming a flow channel fluidly connecting adjacent microcolumns of the microcolumns through which a single liquid sample is desired to pass in a serial manner, and wherein the top channel layer is optionally patterned to work in fluid and serial connection with the bottom capping layer so as to pass the single liquid sample through the microcolumns in a serial manner.

6. The integrated microfluidic cell processing system according to claim 4 further comprising:
   a top port layer proximately disposed on the top capping layer, said top port layer comprising one or more input port each in fluidic alignment with a corresponding microcolumn so as to effectuate introduction of a sample liquid into a desired microcolumn.

7. The integrated microfluidic cell processing system according to claim 4 further comprising:
   a bottom port layer proximately disposed on the bottom capping layer, said bottom port layer comprising one or more outlet port each in fluidic alignment with a corresponding microcolumn so as to effectuate expulsion of a liquid sample from a desired microcolumn.

8. The integrated microfluidic cell processing system according to claim 4 further comprising:
   a top frit gasket layer for aiding the containment of the affinity chromatography agent, wherein said top frit gasket layer is deposited between the top surface of the microcolumn layer and the top capping layer.

9. The integrated microfluidic cell processing system according to claim 4 further comprising:

a top port layer proximately disposed on the top capping layer, said top port layer comprising one or more input port each in fluidic alignment with a corresponding microcolumn so as to effectuate introduction of a sample liquid into a desired microcolumn;

an optional bottom port layer proximately disposed on the bottom capping layer, said bottom port layer comprising one or more outlet port each in fluidic alignment with a corresponding microcolumn so as to effectuate expulsion of a liquid sample from a desired microcolumn; and a top washer layer and/or a bottom washer layer for securing the ports of the top port layer and the optional bottom port layer in alignment with their corresponding microcolumns, wherein said top washer layer is proximately deposited at the top capping layer and comprises a plurality of openings through which the ports of the top port layer protrude, and wherein said bottom washer layer is proximately deposited at the bottom capping layer and comprises a plurality of openings through which the ports of the optional bottom port layer protrude.

10. The integrated microfluidic cell processing system according to claim 4, wherein the affinity chromatography agent comprises an immobilized target molecule selected from the group consisting of a whole cell, a virus, a virus particle, a protein, a modified protein, a polypeptide, a modified polypeptide, an RNA molecule, a DNA molecule, a modified DNA molecule, a polysaccharide, an amino acid, an antibiotic, a pharmaceutical agent, an organic non-pharmaceutical agent, a macromolecular complex, a carbohydrate, a lipid, a small molecule, a chemical compound, a mixture of lysed cells, and a mixture of purified, partially purified, or non-purified protein, and optionally the immobilized target molecule is labeled and/or provided from a mixture of lysed cells, a mixture of purified, partially purified, or non-purified protein.

11. The integrated microfluidic cell processing system according to claim 1, wherein said at least one microfluidic chip is configured for on-chip detection of a presence or absence of a target nucleic acid region in an isolated nucleic acid sample, wherein the nucleic acid entanglement component comprises a plurality of nucleic acid entanglement micropillars configured and arranged in a manner effective to physically entangle and maintain thereon an isolated nucleic acid sample; the at least one microfluidic chip further comprising:

the isolated nucleic acid sample immobilized in the nucleic acid entanglement array; and at least one probe specific to a target nucleic acid region, said at least one probe being specifically bound to the target nucleic acid region and detectable when said isolated nucleic acid sample includes the target nucleic acid region, thereby enabling on-chip analysis of the presence or absence of the target nucleic acid region in the isolated nucleic acid sample.

12. The integrated microfluidic cell processing system according to claim 11, wherein the isolated nucleic acid sample comprises genomic DNA (gDNA), extrachromosomal DNA, chromatin, plasmid DNA, a nucleic acid aptamer, an oligonucleotide, or a nucleic acid biomarker and/or wherein the target nucleic acid region comprises a gene, mutation, or nucleotide sequence from a eukaryotic cell, a human or a non-human animal.

13. The integrated microfluidic cell processing system according to claim 11, wherein the target nucleic acid region comprises a gene, mutation, or nucleotide sequence that is related to or that is a marker for presence or risk of a disease or abnormal condition of a multicellular organism; and/or wherein the target nucleic acid region is specific for a pathogen, antibiotic resistant strain of bacteria, food contaminant, foodborne illness, paternity determination, DNA fingerprinting, or individual identity.

14. The integrated microfluidic cell processing system according to claim 11, wherein the at least one probe comprises a collection of multiple probes with each probe being specific to a unique target nucleic acid region or to another probe which is specific to a unique target nucleic acid region; and optionally the collection of multiple probes comprises a panel of probes effective to produce a genetic profile for a disease or abnormal condition in a multicellular organism.

15. The integrated microfluidic cell processing system according to claim 11, wherein the at least one probe is a fluorescence probe or selected from the group consisting of molecular beacons, peptide nucleic acid probes, aptamers, and protein probes.

16. The integrated microfluidic cell processing system according to claim 1, said system further comprising a liquid collection apparatus comprising well portions for collecting liquid samples from the microcolumns, wherein each well portion is aligned with a single corresponding microcolumn for collection of the liquid sample therefrom.

17. The integrated microfluidic cell processing system according to claim 16, wherein a liquid flow mechanism is programmable to move the liquid samples through the microcolumns at a desired flow rate, at a desired volume, for a desired amount of time, and/or for a desired time interval.

18. The integrated microfluidic cell processing system according to claim 16, wherein a liquid flow mechanism comprises a pump for either pushing or pulling the liquid sample through one or more of the microcolumns.

19. The integrated microfluidic cell processing system according to claim 16, wherein the liquid collection apparatus is a microplate having a plurality of wells for collecting liquid samples from the microcolumns.

20. A method of collecting one or more liquid sample, said method comprising:

providing an integrated microfluidic cell processing system according to claim 16;

running one or more liquid sample through the microcolumns of the affinity microcolumn layer of the system either in a parallel manner or a serial manner under conditions effective to allow a test agent contained in the liquid sample to bind specifically to a target molecule contained in the microcolumns; and recovering from each microcolumn the test agent or test agents that bind specifically to the respective target molecules of each microcolumn, said recovering taking place in the liquid collection apparatus.

* * * * *